United States Patent
Yamada et al.

(10) Patent No.: US 12,035,755 B2
(45) Date of Patent: Jul. 16, 2024

(54) AEROSOL GENERATION DEVICE, AND METHOD AND PROGRAM FOR OPERATING SAME

(71) Applicant: JAPAN TOBACCO INC., Tokyo (JP)

(72) Inventors: Manabu Yamada, Tokyo (JP); Takeshi Akao, Tokyo (JP); Kazuma Mizuguchi, Tokyo (JP); Masayuki Tsuji, Tokyo (JP); Hajime Fujita, Tokyo (JP)

(73) Assignee: JAPAN TOBACCO INC., Tokyo (JP)

( * ) Notice: Subject to any disclaimer, the term of this patent is extended or adjusted under 35 U.S.C. 154(b) by 979 days.

(21) Appl. No.: 16/937,590

(22) Filed: Jul. 24, 2020

(65) Prior Publication Data

US 2020/0352247 A1 Nov. 12, 2020

Related U.S. Application Data

(63) Continuation of application No. PCT/JP2018/002454, filed on Jan. 26, 2018.

(51) Int. Cl.
*A24F 40/53* (2020.01)
*A24F 40/10* (2020.01)
(Continued)

(52) U.S. Cl.
CPC ............ *A24F 40/53* (2020.01); *A24F 40/40* (2020.01); *A24F 40/42* (2020.01); *A24F 40/51* (2020.01);
(Continued)

(58) Field of Classification Search
None
See application file for complete search history.

(56) References Cited

U.S. PATENT DOCUMENTS

2014/0253144 A1 9/2014 Novak, III et al.
2014/0299141 A1 10/2014 Flick
(Continued)

FOREIGN PATENT DOCUMENTS

EP 2399636 A1 12/2011
EP 2257195 B1 6/2012
(Continued)

OTHER PUBLICATIONS

Extended European Search Report issued Feb. 9, 2021, in corresponding European Patent Application No. 18902091.0.
(Continued)

*Primary Examiner* — Philip Y Louie
*Assistant Examiner* — Miles A Simpson
(74) *Attorney, Agent, or Firm* — XSENSUS LLP

(57) ABSTRACT

Provided is an aerosol generation device that can more accurately detect shortage of an aerosol source after a cartridge has been replaced. An aerosol generation device 100A that comprises: a power source 110; a load 132 that has temperature-resistance value characteristics, has a temperature-variable electrical resistance value, and atomizes an aerosol source by generating heat due to supply of power from the power source 110; memory 114 that stores the temperature-resistance value characteristics; a sensor 112 that outputs a value that is related to the resistance value of the load 132; and a control part 106 that, on the basis of the correspondence between the output value from the sensor 112 and an estimated value for the temperature of the load 132 that corresponds to the output value, calibrates the stored temperature-resistance value characteristics.

16 Claims, 17 Drawing Sheets

(51) Int. Cl.
    *A24F 40/20*     (2020.01)
    *A24F 40/40*     (2020.01)
    *A24F 40/42*     (2020.01)
    *A24F 40/51*     (2020.01)
    *A24F 40/57*     (2020.01)
    *A61M 15/06*     (2006.01)

(52) U.S. Cl.
    CPC .............. *A24F 40/57* (2020.01); *A24F 40/10* (2020.01); *A24F 40/20* (2020.01); *A61M 15/06* (2013.01)

(56) References Cited

U.S. PATENT DOCUMENTS

| | | |
|---|---|---|
| 2015/0208729 A1 | 7/2015 | Moonsees et al. |
| 2015/0359263 A1 | 12/2015 | Bellinger |
| 2016/0192706 A1 | 7/2016 | Kananen |
| 2016/0316822 A1 | 11/2016 | Liu |
| 2017/0055585 A1 | 3/2017 | Fursa et al. |
| 2017/0347717 A1 | 12/2017 | Matsumo et al. |
| 2018/0027878 A1 * | 2/2018 | Dendy ................ H01M 50/247 |
| 2018/0070641 A1 | 3/2018 | Batista et al. |
| 2018/0352864 A1 | 12/2018 | Takeuchi et al. |
| 2021/0007393 A1 * | 1/2021 | Jung .................... A24F 40/465 |

FOREIGN PATENT DOCUMENTS

| | | |
|---|---|---|
| EP | 2471392 A1 | 7/2012 |
| EP | 2 654 469 A0 | 10/2013 |
| EP | 1412829 B1 | 3/2014 |
| EP | 2654469 B1 | 3/2017 |
| EP | 2797446 B1 | 10/2017 |
| GB | 2533651 A | 6/2016 |
| GB | 2542925 A | 4/2017 |
| JP | 2003-241565 A | 8/2003 |
| JP | 2016-513453 A | 5/2016 |
| JP | 2016-524777 A | 8/2016 |
| JP | 2016-531549 A | 10/2016 |
| JP | 2017-501805 A | 1/2017 |
| JP | 2017-503520 A | 2/2017 |
| WO | 2014/040988 A2 | 3/2014 |
| WO | 2015/100361 A1 | 7/2015 |
| WO | 2015/138560 A1 | 9/2015 |
| WO | 2016/143079 A1 | 9/2016 |
| WO | 2016/150922 A2 | 9/2016 |
| WO | 2017/084818 A1 | 5/2017 |
| WO | 2017/141979 A1 | 8/2017 |

OTHER PUBLICATIONS

International Search Report and Written Opinion mailed on Apr. 24, 2018 for PCT/JP2018/002439 filed on Jan. 26, 2018, 9 pages including English Translation of the International Search Report.
International Search Report and Written Opinion mailed on Apr. 24, 2018 for PCT/JP2018/002436 filed on Jan. 26, 2018, 9 pages including English Translation of the International Search Report.
International Search Report and Written Opinion mailed on Apr. 24, 2018 for PCT/JP2018/002454 filed on Jan. 26, 2018, 9 pages including English Translation of the International Search Report.
Extended European Search Report issued Feb. 11, 2021, in corresponding European Patent Application No. 18902399.7.
Extended European Search Report issued Feb. 15, 2021, in corresponding European Patent Application No. 18902789.9.
U.S. Office Action issued Aug. 17, 2023 in U.S. Appl. No. 16/937,585, 29 pages.
U.S. Office Action issued Aug. 23, 2023 in U.S. Appl. No. 16/937,614, 30 pages.
Action issued Sep. 29, 2023 in Chinese Patent Application No. 201880087672.7, 27 pages.
Final U.S. Office Action issued in co-pending U.S. Appl. No. 16/937,585 29 pages Feb. 15, 2024.

* cited by examiner

AEROSOL GENERATION DEVICE, AND METHOD AND PROGRAM FOR OPERATING SAME

CROSS REFERENCE TO RELATED APPLICATIONS

The present application is a continuation application of International Application No. PCT/JP2018/002454, filed on Jan. 26, 2018. This application is related to U.S. Ser. No. 16/937,585, filed on Jul. 24, 2020; entitled: AEROSOL GENERATION DEVICE, AND METHOD AND PROGRAM FOR OPERATING SAME and U.S. Ser. No. 16/937,614, filed on Jul. 24, 2020; entitled AEROSOL GENERATION DEVICE, AND METHOD AND PROGRAM FOR OPERATING SAME.

TECHNICAL FIELD

The present disclosure relates to an aerosol generation device that generates aerosol to be inhaled by a user, and a method and a program for actuating the same.

BACKGROUND ART

In an aerosol generation device such as a general electronic cigarette, a heated cigarette, or nebulizer, the aerosol generation device being configured to generate aerosol to be inhaled by a user, if the user performs inhalation when an aerosol source to be atomized to generate the aerosol is insufficient in quantity, a sufficient quantity of aerosol cannot be supplied to the user. In addition, in the case of the electronic cigarette or the heated cigarette, there is a problem in that the aerosol having an unintended inhaling flavor may be emitted.

As a solution to this problem, PTL 1 discloses a technique for detecting the presence of an aerosol source based on electric power required to maintain a temperature of a heater configured to heat the aerosol source. PTL 2 discloses an aerosol generation device having a shunt circuit in addition to an aerosol generating circuit. PTL 3 discloses a technique for reading, on a power supply side, information carried by a cartridge for storing an aerosol source and performing the control based on this information. PTL 4 to PTL 12 also disclose various techniques that solve the above-described problem or may contribute to the solution of the above-described problem.

However, the conventional techniques require components including an ammeter and a voltmeter to detect insufficiency of an aerosol source, resulting in increases in cost, weight and size of the device and the like. In addition, the conventional techniques use a parameter variable depending on errors of the components of the device, which causes low detection accuracy with respect to the insufficiency of the aerosol source. Furthermore, it is necessary to develop the technique for detecting the insufficiency of the aerosol source with higher accuracy after the cartridge is replaced.

CITATION LIST

Patent Literature

PTL 1: European Patent Application Publication No. 2797446
PTL 2: European Patent Application Publication No. 1412829
PTL 3: International Publication No. WO 2015/138560
PTL 4: European Patent Application Publication No. 2471392
PTL 5: European Patent Application Publication No. 2257195
PTL 6: European Patent Application Publication No. 2654469
PTL 7: International Publication No. WO 2015/100361
PTL 8: Japanese Translation of PCT International Application Publication No. 2017-503520
PTL 9: International Publication No. WO 2017/084818
PTL 10: European Patent Application Publication No. 2399636
PTL 11: Japanese Translation of PCT International Application Publication No. 2016-531549
PTL 12: International Publication No. WO 2016/143079

SUMMARY OF INVENTION

Technical Problem

The present disclosure has been devised in view of the point described above.

A first problem to be solved by the present disclosure is to provide an aerosol generation device with a smaller number of components to be required and with high detection accuracy with respect to insufficiency of an aerosol source, and a method and a program for actuating the same.

A second problem to be solved by the present disclosure is to provide an aerosol generation device that suppresses an influence of product errors of components on detection accuracy with respect to insufficiency of an aerosol source, and a method of manufacturing the aerosol generation device.

A third problem to be solved by the present disclosure is to provide an aerosol generation device that can detect insufficiency of an aerosol source with higher accuracy after a cartridge is replaced, and a method and a program for actuating the same.

Solution to Problem

In order to solve the first problem described above, according to a first embodiment of the present disclosure, there is provided an aerosol generation device comprising a power supply, a storage unit that stores an aerosol source or an aerosol base material that retains the aerosol source, a load that generates heat upon receipt of electric power from the power supply and atomizes the aerosol source supplied from the storage unit or retained in the aerosol base material using the heat, and in which an electric resistance value of the load changes in response to a temperature, a circuit that electrically connects the power supply and the load, and a control unit configured to determine whether the aerosol source that is capable of being supplied from the storage unit or is retained in the aerosol base material is insufficient in quantity based on a first voltage value which is a value of a voltage applied to an entire circuit and a second voltage value which is a value of a voltage applied to a portion in the circuit where the voltage to be applied changes according to changes in temperature of the load.

In an embodiment, the control unit is configured to determine that the aerosol source is insufficient in quantity when the second voltage value satisfies a first condition a plurality of times while the first voltage value is controlled to be constant or when the electric resistance value of the load derived from the first voltage value and the second voltage value satisfies a second condition a plurality of times.

In an embodiment, the control unit is configured to determine that the aerosol source is insufficient in quantity when the first condition is continuously satisfied a plurality of times or when the second condition is continuously satisfied a plurality of times.

In an embodiment, the control unit is configured to store the number of times that the first condition is satisfied or the number of times that the second condition is satisfied, and to decrease the number of times when the first condition is not satisfied or when the second condition is not satisfied.

In an embodiment, the control unit is configured to return the number of times to an initial value when the first condition is not satisfied or when the second condition is not satisfied.

In an embodiment, the aerosol generation device comprises a connecter that allows attachment/detachment of a cartridge including the storage unit or an aerosol generating article including the aerosol base material and that allows detection of the attachment/detachment of the cartridge or the aerosol generating article. The control unit is configured to store the number of times that the first condition is satisfied or the number of times that the second condition is satisfied, and to decrease the number of times when the cartridge or the aerosol generating article is attached to the connecter.

In an embodiment, identification information or a usage history of the cartridge or the aerosol generating article is capable of being acquired in a predetermined manner. The control unit is configured to determine whether to decrease the number of times based on the identification information or the usage history of the cartridge or the aerosol generating article that is attached to the connecter.

In an embodiment, the control unit is configured to store the number of times that the first condition is satisfied or the number of times that the second condition is satisfied, to determine whether the aerosol source is insufficient in quantity based on comparison between the number of times and a predetermined threshold, and not to increase the number of times, to reduce an increase amount of the number of times or to increase the predetermined threshold when the first condition or the second condition is satisfied in a state in which a time-series change of a demand for generation of aerosol does not meet a predetermined normal change.

In an embodiment, the control unit is configured to determine whether the aerosol source is insufficient in quantity using a first reference based on the first voltage value and the second voltage value and a second reference different from the first reference, and to determine that the aerosol source is insufficient in quantity when the first reference is satisfied a plurality of times or when the second reference is satisfied a smaller number of times than the plurality of times.

In an embodiment, it is more difficult to satisfy the second reference than the first reference.

In an embodiment, the first reference is whether the second voltage value satisfies a first threshold while the first voltage value is controlled to be constant, or whether an electric resistance value of the load derived from the first voltage value and the second voltage value satisfies a second threshold. The second reference is whether the second voltage value satisfies a threshold greater than the first threshold or whether the electric resistance value of the load satisfies a threshold greater than the second threshold.

In an embodiment, the control unit is configured to determine whether the second reference is satisfied before determining whether the first reference is satisfied.

In an embodiment, the control unit is configured to perform at least one of stop of supply of the electric power from the power supply to the load or notification to a user without determining whether the first reference is satisfied when the second reference is satisfied and it is determined that the aerosol source is insufficient in quantity.

In an embodiment, the aerosol generation device comprises a conversion unit that converts an output voltage of the power supply and outputs the converted voltage to apply it to the entire circuit. The control unit is configured to control the conversion unit.

In an embodiment, the control unit is configured to control the conversion unit to output a constant voltage when determining whether the aerosol source is insufficient in quantity.

In an embodiment, the aerosol generation device comprises a sensor that outputs the second voltage value. The control unit is configured to determine whether the aerosol source is insufficient in quantity based on the first voltage value which is a value of the constant voltage and the second voltage value which is output from the sensor.

In an embodiment, the control unit is configured to determine whether the aerosol source is insufficient in quantity based on comparison between the second voltage value output from the sensor and a predetermined threshold.

In an embodiment, the aerosol generation device comprises a first sensor and a second sensor that output the first voltage value and the second voltage value, respectively. The control unit is configured to determine whether the aerosol source is insufficient in quantity based on comparison between an electric resistance value of the load derived from output values from the first sensor and the second sensor and a predetermined threshold.

In an embodiment, the aerosol generation device comprises a known resistor that is connected in series with the load and has a known electric resistance value. The second voltage value is a value of a voltage applied to the load or the known resistor.

In an embodiment, the known resistor has an electric resistance value higher than an electric resistance value of the load. The aerosol generation device comprises a sensor that outputs the second voltage value based on comparison between a reference voltage and an amplified voltage applied to the load.

According to the first embodiment of the present disclosure, there is provided a method of actuating an aerosol generation device, the method comprising the steps of atomizing an aerosol source using heat generated by supplying electric power from a power supply to a load in which an electric resistance value changes in response to a temperature, and determining whether the aerosol source capable of being supplied to generate aerosol is insufficient in quantity based on a first voltage value which is a value of a voltage applied to an entire circuit that electrically connects the power supply and the load and a second voltage value which is a value of a voltage applied to a portion in the circuit where the voltage to be applied changes according to changes in temperature of the load.

According to the first embodiment of the present disclosure, there is provided an aerosol generation device comprising a power supply, a storage unit that stores an aerosol source or an aerosol base material that retains the aerosol source, a load that generates heat upon receipt of electric power from the power supply and atomizes the aerosol source supplied from the storage unit or retained in the aerosol base material using the heat, and in which an electric resistance value of the load changes in response to a temperature, a circuit that electrically connects the power supply and the load, and a control unit configured to estimate a residual quantity of the aerosol source stored by the storage unit or retained in the aerosol base material based on a first voltage value which is a value of a voltage applied to an entire circuit and a second voltage value which is a value of a voltage applied to a portion in the circuit where the voltage to be applied changes according to changes in temperature of the load.

According to the first embodiment of the present disclosure, there is provided a method of actuating an aerosol generation device, the method comprising the steps of atomizing an aerosol source using heat generated by supplying electric power from a power supply to a load in which an electric resistance value changes in response to a temperature, and estimating a residual quantity of the aerosol source based on a first voltage value which is a value of a voltage applied to an entire circuit that electrically connects the power supply and the load and a second voltage value which is a value of a voltage applied to a portion in the circuit where the voltage to be applied changes according to changes in temperature of the load.

According to the first embodiment of the present disclosure, there is provided an aerosol generation device comprising a power supply, a storage unit that stores an aerosol source or an aerosol base material that retains the aerosol source, a load that generates heat upon receipt of electric power from the power supply and atomizes the aerosol source supplied from the storage unit or retained in the aerosol base material using the heat, a circuit that electrically connects the power supply and the load, and a control unit configured to determine whether the aerosol source that is capable of being supplied from the storage unit to the load or is retained in the aerosol base material is insufficient in quantity based on a first voltage value which is a value of a voltage applied to an entire circuit and a second voltage value which is a value of a voltage applied to a portion in the circuit, wherein the control unit is configured to acquire the first voltage value from a memory and the second voltage value from a sensor.

According to the first embodiment of the present disclosure, there is provided a method of actuating an aerosol generation device, the method comprising the steps of atomizing an aerosol source using heat generated by supplying electric power from a power supply to a load, and determining whether the aerosol source capable of being supplied to generate aerosol is insufficient in quantity based on a first voltage value which is a value of a voltage applied to an entire circuit that electrically connects the power supply and the load and a second voltage value which is a value of a voltage applied to a portion in the circuit, wherein the first voltage value is acquired from a memory and the second voltage value is acquired from a sensor.

According to the first embodiment of the present disclosure, there is provided an aerosol generation device comprising a power supply, a storage unit that stores an aerosol source or an aerosol base material that retains the aerosol source, a load that generates heat upon receipt of electric power from the power supply and atomizes the aerosol source using the heat, a circuit that electrically connects the power supply and the load, and a control unit configured to estimate a residual quantity of the aerosol source stored by the storage unit or retained in the aerosol base material based on a first voltage value which is a value of a voltage applied to an entire circuit and a second voltage value which is a value of a voltage applied to a portion in the circuit, wherein the control unit is configured to acquire the first voltage value from a memory and the second voltage value from a sensor.

According to the first embodiment of the present disclosure, there is provided a method of actuating an aerosol generation device, the method comprising the steps of atomizing an aerosol source using heat generated by supplying electric power from a power supply to a load, and estimating a residual quantity of the aerosol source based on a first voltage value which is a value of a voltage applied to an entire circuit that electrically connects the power supply and the load and a second voltage value which is a value of a voltage applied to a portion in the circuit, wherein the first voltage value is acquired from a memory and the second voltage value is acquired from a sensor.

According to the first embodiment of the present disclosure, there is provided a program for, when being executed by a processor, causing the processor to perform any of the above-described methods.

In order to solve the second problem described above, according to a second embodiment of the present disclosure, there is provided an aerosol generation device comprising a power supply, a load that generates heat upon receipt of electric power from the power supply and atomizes an aerosol source using the heat, and in which an electric resistance value of the load changes in response to a temperature, a first circuit used to cause the load to atomize the aerosol source, a second circuit used to detect a voltage that changes according to changes in temperature of the load, connected to the first circuit in parallel, and having an electric resistance value higher than an electric resistance value of the first circuit, an acquisition unit that acquires a value of a voltage applied to the second circuit and the load, and a sensor that outputs a value of the voltage that changes according to the changes in the temperature of the load.

In an embodiment, the second circuit comprises a known resistor that is connected in series with the load and has a known electric resistance value. The sensor outputs a value of a voltage applied to the load or the known resistor as the value of the voltage that changes according to changes in temperature of the load.

In an embodiment, the known resistor has an electric resistance value higher than an electric resistance value of the load, and the sensor outputs the value of the voltage applied to the load.

In an embodiment, the value of the voltage that changes according to the changes in the temperature of the load is obtained based on comparison between a value of a reference voltage and a value of an amplified voltage applied to the load.

In an embodiment, the aerosol generation device comprises a conversion unit that converts an output voltage of the power supply and outputs the converted voltage to apply it to the second circuit and the load. The acquisition unit acquires a target value of an output voltage of the conversion unit while a current flows through the second circuit.

In an embodiment, the conversion unit is connected between a higher voltage node of nodes to which the first circuit and the second circuit are connected and the power supply.

In an embodiment, the conversion unit is a switching regulator that is capable of decreasing and outputting an input voltage.

In an embodiment, a storage unit that stores the aerosol source and the load are included in a cartridge that is attachable/detachable to/from the aerosol generation device, via a connecter. The sensor is not included in the cartridge.

In an embodiment, the second circuit comprises a known resistor that is connected in series with the load and has a known electric resistance value. A storage unit that stores the aerosol source and the load are included in a cartridge that is attachable/detachable to/from the aerosol generation device, via a connecter. The sensor outputs a value of a voltage applied to the load and the connecter as the value of the voltage that changes according to the changes in the temperature of the load.

In an embodiment, an aerosol base material that retains the aerosol source is included in an aerosol generating article that is insertable/extractable into/from the aerosol generation device. The sensor is not included in the aerosol generating article.

In an embodiment, the known resistor has such an electric resistance value that a current having magnitude that allows distinguishing between a state in which the current flows through the second circuit and a state in which no current flows through the second circuit flows through the second circuit.

In an embodiment, the known resistor has such an electric resistance value that the current having the magnitude that allows distinguishing between the state in which the current flows through the second circuit and a state in which no current flows through the second circuit flows through the second circuit in a case where a voltage of the power supply is a discharge termination voltage.

In an embodiment, the aerosol generation device comprises a conversion unit that converts an output voltage of the power supply and outputs the converted voltage to apply it to the second circuit and the load. The known resistor has such an electric resistance value that the current having magnitude that allows distinguishing between the state in which the current flows through the second circuit and the state in which no current flows through the second circuit flows through the second circuit in a case where an output voltage of the conversion unit is applied to the second circuit and the load.

In an embodiment, the known resistor has such an electric resistance value that the current having the magnitude that allows distinguishing between the state in which the current flows through the second circuit and the state in which no current flows through the second circuit flows through the second circuit in a case where the temperature of the load is an achievable temperature only when the aerosol source is insufficient in quantity.

In an embodiment, the known resistor has such an electric resistance value that only electric power required for heat retention of the load is supplied to the load while a current flows through the second circuit.

In an embodiment, the known resistor has such an electric resistance value that the load does not generate aerosol while a current flows through the second circuit.

In an embodiment, the aerosol generation device comprises a first switch that connects and disconnects electrical conduction of the first circuit, a second switch that connects and disconnects the electrical conduction of the second circuit, and a control unit configured to control switching of the first switch and the second switch so that an on time of the first switch is longer than an on time of the second switch.

In an embodiment, the on time of the second switch is a minimum time period that is achievable by the control unit.

According to the second embodiment of the present disclosure, there is provided a method of manufacturing an aerosol generation device, the method comprising the steps of arranging a power supply, atomizing an aerosol source using heat generated by supplying electric power from the power supply and arranging a load in which an electric resistance value changes in response to a temperature, forming a first circuit used to cause the load to atomize the aerosol source, forming a second circuit used to detect a voltage that changes according to changes in temperature of the load, connected to the first circuit in parallel, and having an electric resistance value higher than an electric resistance value of the first circuit, arranging an acquisition unit that acquires a value of a voltage applied to the second circuit and the load, and arranging a sensor that outputs a value of the voltage that changes according to the changes in the temperature of the load.

In order to solve the third problem described above, according to a third embodiment of the present disclosure, there is provided an aerosol generation device comprising a power supply, a load that generates heat upon receipt of electric power from the power supply and atomizes an aerosol source using the heat, and has a temperature-resistance value characteristic in which an electric resistance value of the load changes in response to a temperature, a memory that stores the temperature-resistance value characteristic, a sensor that outputs a value related to a resistance value of the load, and a control unit configured to calibrate the stored temperature-resistance value characteristic based on correspondence between an output value of the sensor and an estimate of a temperature of the load corresponding to the output value.

In an embodiment, the control unit is configured to calibrate the stored temperature-resistance value characteristic based on correspondence between the output value of the sensor before the load generates aerosol and a room temperature.

In an embodiment, the control unit is configured to calibrate the stored temperature-resistance value characteristic based on the correspondence between the output value of the sensor before the load generates the aerosol and the room temperature, when a predetermined condition by which it is determined that the temperature of the load is the room temperature is established.

In an embodiment, the predetermined condition is that a predetermined period of time has elapsed since previous aerosol generation.

In an embodiment, the aerosol generation device comprises a cartridge that includes the load and a storage unit that stores the aerosol source or an aerosol generating article that includes the load and an aerosol base material that retains the aerosol source, and a connecter that allows attachment/detachment of the cartridge or insertion/extraction of the aerosol generating article. The predetermined condition is that a predetermined period of time has elapsed since the attachment of the cartridge to the connecter or the insertion of the aerosol generating article into the connecter.

In an embodiment, the sensor is configured to output any one of a temperature of the power supply, a temperature of the control unit, a temperature inside the aerosol generation device and an ambient temperature of the aerosol generation device. The predetermined condition may be that a temperature output by the sensor becomes the room temperature or an absolute value of a difference between the temperature output by the sensor and the room temperature is equal to or less than a predetermined threshold.

In an embodiment, the control unit is configured to control supply of electric power from the power supply to the load, and to control the load not to generate the aerosol until the output value of the sensor is associated with an estimate of a temperature corresponding to the output value, when the predetermined condition is satisfied.

In an embodiment, the control unit is configured to control to supply predetermined electric power from the power supply to the load, the predetermined electric power being smaller than electric power required to increase the temperature of the load to a temperature at which the load is capable of generating the aerosol, and to calibrate the temperature-resistance value characteristic based on the output value of the sensor while the predetermined electric power is supplied to the load.

In an embodiment, the predetermined electric power is electric power that does not cause the temperature of the load to increase over resolution of the sensor.

In an embodiment, the predetermined electric power is electric power that does not cause the temperature of the load to increase.

In an embodiment, the control unit is configured to control supply of electric power from the power supply to the load, and to calibrate the stored temperature-resistance value characteristic based on correspondence between the output value of the sensor when electric power sufficient for aerosol generation is supplied to the load and a temperature causing the aerosol generation.

In an embodiment, the control unit is configured not to calibrate the stored temperature-resistance value characteristic when the output value of the sensor when the electric power sufficient for the aerosol generation is supplied to the load is equal to or higher than a threshold or when a change amount in the output value of the sensor when predetermined electric power is supplied to the load is equal to or higher than a threshold.

In an embodiment, the control unit is configured to control supply of electric power from the power supply to the load, and to calibrate the stored temperature-resistance value characteristic based on correspondence between the output value of the sensor when electric power sufficient for aerosol generation is supplied to the load and is in a steady state at a value other than a room temperature, and a temperature causing the aerosol generation.

In an embodiment, a temperature and the electric resistance value of the load are in a proportional relationship, and the control unit is configured to calibrate an intercept of the stored temperature-resistance value characteristic.

In an embodiment, a temperature and the electric resistance value of the load are in a proportional relationship. The aerosol generation device comprises a database that stores the electric resistance value of the load and one of an inclination and an intercept of the temperature-resistance value characteristic, for each type of the load. The control unit is configured to calibrate the one of the inclination and the intercept of the temperature-resistance value characteristic based on the output value of the sensor and the database, and to calibrate the other of the inclination and the intercept of the temperature-resistance value characteristic based on the output value of the sensor and the calibrated one of the inclination and the intercept of the temperature-resistance value characteristic.

In an embodiment, the database stores the electric resistance value of the load at a room temperature or a temperature at which aerosol is generated and the other of the inclination and an intercept of the temperature-resistance value characteristic, for each type of the load.

In an embodiment, a temperature and the electric resistance value of the load are in a proportional relationship. The control unit is configured to calibrate an inclination and an intercept of the stored temperature-resistance value characteristic based on the correspondence between the output value of the sensor and an estimate of the temperature of the load corresponding to the output value, and information about the load or a cartridge including the load.

In an embodiment, the control unit is configured to acquire the information about the load or the cartridge from at least one of communication with an external terminal, identification information of the load, identification information of the cartridge or a package of the cartridge, and a user input.

In an embodiment, a temperature and an electric resistance value of the load are in a proportional relationship. The control unit is configured to calibrate an inclination and an intercept of the stored temperature-resistance value characteristic based on correspondence between the output value of the sensor before the load generates aerosol and a room temperature and correspondence between the output value of the sensor when electric power sufficient for aerosol generation is supplied to the load and a temperature causing the aerosol generation.

In an embodiment, the control unit is configured not to calibrate the stored temperature-resistance value characteristic when the output value of the sensor when the electric power sufficient for the aerosol generation is supplied to the load is equal to or higher than a threshold or when a change amount in the output value of the sensor when predetermined electric power is supplied to the load is equal to or higher than the threshold.

In an embodiment, the aerosol generation device comprises a cartridge that includes the load and a storage unit that stores the aerosol source or an aerosol generating article that includes the load and an aerosol base material that retains the aerosol source, and a connecter that allows attachment/detachment of the cartridge or insertion/extraction of the aerosol generating article. The control unit is configured to calibrate the stored temperature-resistance value characteristic only when detecting the detachment of the cartridge from the connector or the extraction of the aerosol generating article from the connecter.

In an embodiment, the control unit is configured to determine whether to perform a calibration based on a predetermined condition, prior to the calibration of the stored temperature-resistance value characteristic.

In an embodiment, the aerosol generation device comprises a cartridge that includes the load and a storage unit that stores the aerosol source or an aerosol generating article that includes the load and an aerosol base material that retains the aerosol source, and a connecter that allows attachment/detachment of the cartridge or insertion/extraction of the aerosol generating article. The control unit is configured to store a resistance value of the cartridge detached from the connector or a resistance value of the aerosol generating article extracted from the connecter. The predetermined condition is that the resistance value stored by the control unit is different from the resistance value of the cartridge newly attached to the connector or the resistance value of the aerosol generating article newly inserted into the connecter.

In an embodiment, the predetermined condition is that a rate of change in the resistance value of the cartridge attached to the connecter or a rate of change in the resistance value of the aerosol generating article inserted into the connecter is lower than a predetermined threshold while power supply to the load is continued.

In an embodiment, the predetermined condition is that from the correspondence between the output value of the sensor and an estimate of the temperature of the load corresponding to the output value, it is determined that the temperature of the load is estimated smaller than an actual value if the stored temperature-resistance value characteristic is not calibrated.

In an embodiment, the predetermined condition is that the output value of the sensor is smaller than a predetermined threshold.

In an embodiment, the aerosol generation device comprises a cartridge that includes the load and a storage unit that stores the aerosol source or an aerosol generating article that includes the load and an aerosol base material that retains the aerosol source, and a connecter that allows attachment/detachment of the cartridge or insertion/extraction of the aerosol generating article. The sensor is not included in the cartridge or the aerosol generating article. The control unit is configured to calibrate the stored temperature-resistance value characteristic based on correspondence between a value obtained by subtracting a predetermined value from the output value of the sensor and the estimate of the temperature of the load corresponding to the output value.

In an embodiment, the aerosol generation device comprises a first circuit used to cause the load to atomize the aerosol source, and a second circuit used to detect a value related to a resistance value of the load, connected to the first circuit in parallel, and having an electric resistance value higher than an electric resistance value of the first circuit.

In an embodiment, the aerosol generation device comprises a circuit that electrically connects the power supply and the load. The sensor outputs at least a value of a voltage applied to a portion in the circuit where the voltage to be applied changes according to changes in the temperature of the load. The control unit is configured to derive the electric resistance value of the load based on a value of a voltage applied to an entire circuit and the output value of the sensor.

In an embodiment, the aerosol generation device comprises a conversion unit that converts an output voltage of the power supply and outputs the converted voltage to apply it to the entire circuit. The control unit is configured to control the conversion unit to apply a constant voltage to the entire circuit to derive the electric resistance value of the load.

According to the third embodiment of the present disclosure, there is provided a method of actuating an aerosol generation device, the method comprising the steps of atomizing an aerosol source using heat generated by supplying electric power to a load having a temperature-resistance value characteristic in which an electric resistance value of the load changes in response to a temperature, and calibrating the temperature-resistance value characteristic stored in a memory based on correspondence between an output value of a sensor that outputs a value related to a resistance value of the load and an estimate of a temperature of the load corresponding to the output value.

According to the third embodiment of the present disclosure, there is provided an aerosol generation device comprises a power supply, a load that generates heat upon receipt of electric power from the power supply and atomizes an aerosol source using the heat, and has a temperature-resistance value characteristic in which an electric resistance value of the load changes in response to a temperature, a memory that stores the temperature-resistance value characteristic, a sensor that outputs a value related to a resistance value of the load, and a control unit configured to perform a predetermined control based on the temperature-resistance value characteristic, wherein the control unit is configured to calibrate a value related to the predetermined control based on correspondence between an output value of the sensor and an estimate of a temperature of the load corresponding to the output value.

According to the third embodiment of the present disclosure, there is provided a method of actuating an aerosol generation device, the method comprising the steps of atomizing an aerosol source using heat generated by supplying electric power to a load having a temperature-resistance value characteristic in which an electric resistance value of the load changes in response to a temperature, performing a predetermined control based on the temperature-resistance value characteristic, and calibrating a value related to the predetermined control based on correspondence between an output value of a sensor that output a value related to a resistance value of the load and an estimate of a temperature of the load corresponding to the output value.

According to the third embodiment of the present disclosure, there is provided a program for, when being executed by a processor, causing the processor to perform any of the above-described methods.

Advantageous Effects of Invention

According to the first embodiment of the present disclosure, there can be provided an aerosol generation device with a smaller number of components to be required and with high detection accuracy with respect to insufficiency of an aerosol source, and a method and a program for actuating the same.

According to the second embodiment of the present disclosure, there can be provided an aerosol generation device that suppresses an influence of product errors of components on detection accuracy with respect to insufficiency of an aerosol source.

According to the third embodiment of the present disclosure, there can be provided an aerosol generation device that can detect insufficiency of an aerosol source with higher accuracy after a cartridge is replaced, and a method and a program for actuating the same.

FIG. 14 is a flowchart of exemplary processing of calibrating a temperature-resistance value characteristic of the load according to an embodiment of the present disclosure.

FIG. 15 is a graph showing an example of the temperature-resistance value characteristic of each of different loads that are made of different metals.

DESCRIPTION OF EMBODIMENTS

Hereinafter, embodiments of the present disclosure will be described in detail with reference to the drawings. Note that the embodiments of the present disclosure include an electronic cigarette, a heated cigarette, and a nebulizer, but are not limited to the electronic cigarette, the heated cigarette, and the nebulizer. The embodiments of the present disclosure can include various aerosol generation devices for generating aerosol to be inhaled by a user.

FIG. 1A is a schematic block diagram of a configuration of an aerosol generation device 100A according to an embodiment of the present disclosure. It should be noted that FIG. 1A schematically and conceptually illustrates components included in the aerosol generation device 100A and does not illustrate strict disposition, shapes, dimensions, positional relations, and the like of the components and the aerosol generation device 100A.

As illustrated in FIG. 1A, the aerosol generation device 100A includes a first member 102 (hereinafter, referred to as a "main body 102") and a second member 104A (hereinafter, referred to as a "cartridge 104A"). As illustrated in the figure, as an example, the main body 102 may include a control unit 106, a notifying unit 108, a power supply 110, a sensor 112, and a memory 114. The aerosol generation device 100A may include sensors such as a flow sensor, a pressure sensor, and a voltage sensor, and these sensors are collectively referred to as the "sensor 112" in the present disclosure. The main body 102 may also include a circuit 134 described later. As an example, the cartridge 104A may include a storage unit 116A, an atomizing unit 118A, an air intake channel 120, an aerosol flow path 121, a mouthpiece unit 122, a retention unit 130, and a load 132. Some of the components included in the main body 102 may be included in the cartridge 104A. Some of the components included in the cartridge 104A may be included in the main body 102. The cartridge 104A may be configured to be detachably attached to the main body 102. Alternatively, all the components included in the main body 102 and the cartridge 104A may be included in the same housing instead of the main body 102 and the cartridge 104A.

The storage unit 116A may be configured as a tank that stores the aerosol source. In this case, the aerosol source is liquid, for example, polyalcohol such as glycerin or propylene glycol, or water. When the aerosol generation device 100A is an electronic cigarette, the aerosol source in the storage unit 116A may include a tobacco raw material that emits an inhaling flavor component by being heated or an extract deriving from the tobacco raw material. The retention unit 130 retains the aerosol source. For example, the retention unit 130 is formed of a fibrous or porous material, and retains the aerosol source, which is liquid, in gaps among fibers or thin holes of a porous material. For example, cotton, glass fiber, a tobacco raw material or the like can be used as the above-mentioned fibrous or porous material. When the aerosol generation device 100A is a medical inhaler such as a nebulizer, the aerosol source may also include a drug to be inhaled by a patient. As another example, the storage unit 116A may have a configuration in which a consumed aerosol source can be replenished. Alternatively, the storage unit 116A itself may be configured to be replaceable when the aerosol source is consumed. The aerosol source is not limited to liquid, and may be solid. When the aerosol source is solid, the storage unit 116A may be a hollow container.

The atomizing unit 118A is configured to atomize the aerosol source and generate aerosol. When an inhaling operation is detected by the sensor 112, the atomizing unit 118A generates the aerosol. For example, the inhaling operation may be detected by the flow sensor or a flow rate sensor. In this case, if an absolute value or an amount of change of a flow rate or a flow velocity of air in the air intake channel 120 satisfies a predetermined condition, the air being generated in the air intake channel 120 when the user holds the mouthpiece unit 112 in the user's mouth and performs the inhalation, the flow sensor or the flow rate sensor may detect the inhaling operation. Alternatively, for example, the inhaling operation may be detected by the pressure sensor. In this case, if a predetermined condition is satisfied such as the pressure inside the air intake channel 120 becomes negative when the user holds the mouthpiece unit 112 in the user's mouth and performs the inhalation, the pressure sensor may detect the inhaling operation. Note that the flow sensor, the flow rate sensor and the pressure sensor may be configured to only output a flow rate, a flow velocity, and a pressure in the air intake channel 120, respectively, so that the control unit 106 detects the inhaling operation based on the output.

Alternatively, the atomizing unit 118A may generate the aerosol or the atomizing unit 118A may receive the electric power from the power supply 110 with the use of, for example, a push button, a touch panel, or an acceleration sensor, so that it is unnecessary to detect the inhaling operation or wait detection of the inhaling operation. Such a configuration enables the atomizing unit 118A to appropriately generate the aerosol at a timing when the user actually inhales the aerosol even when the thermal capacity of the retention unit 130 and the load 132 that form the atomizing unit 118A or the thermal capacity of the aerosol source itself is large, for example. Note that the sensor 112 may include a sensor that detects the operation on the push button or the touch panel, or the acceleration sensor.

Figure 1A:
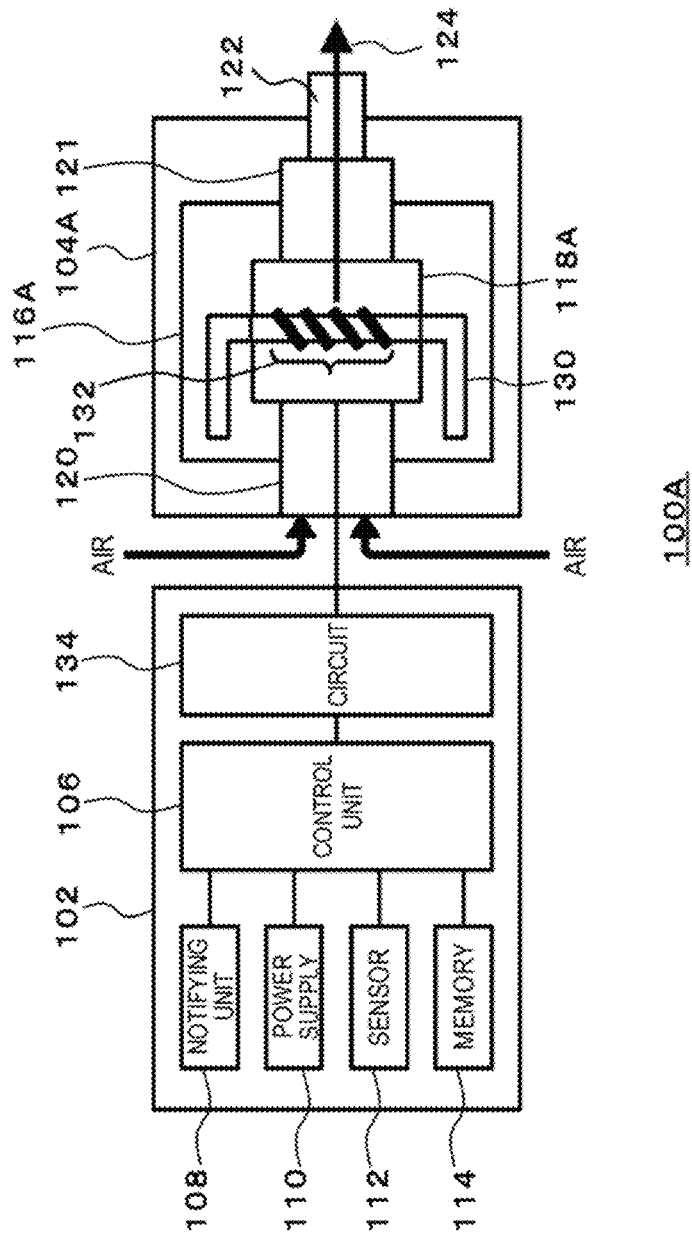
FIG. 1A is a schematic block diagram of a configuration of an aerosol generation device according to an embodiment of the present disclosure.

For example, the retention unit 130 is provided to couple the storage unit 116A and the atomizing unit 118A. In this case, a part of the retention unit 130 communicates with the inside of the storage unit 116A and is in contact with the aerosol source. Another part of the retention unit 130 extends to the atomizing unit 118A. Note that the other part of the retention unit 130 extending to the atomizing unit 118A may be accommodated in the atomizing unit 118, or may communicate with the inside of the storage unit 116A again through the atomizing unit 118A. The aerosol source is carried from the storage unit 116A to the atomizing unit 118A by a capillary effect of the retention unit 130. As an example, the atomizing unit 118A includes a heater including the load 132 that is electrically connected to the power supply 110. The heater is disposed in contact with or in close contact with the retention unit 130. When an inhaling operation is detected, the control unit 106 controls the heater of the atomizing unit 118A or the power supply to the heater, and heats the aerosol source carried through the retention unit 130 to thereby atomize the aerosol source. Another example of the atomizing unit 118A may be an ultrasonic atomizer that atomizes the aerosol source by ultrasonic vibration. The air intake channel 120 is connected to the atomizing unit 118A, and communicates with the outside of the aerosol generation device 100A. The aerosol generated in the atomizing unit 118A is mixed with air taken in via the air intake channel 120. Mixed fluid of the aerosol and the air is delivered to the aerosol flow path 121 as indicated by an arrow 124. The aerosol flow path 121 has a tubular structure for transporting, to the mouthpiece unit 122, the mixed fluid of the aerosol generated in the atomizing unit 118A and the air.

The mouthpiece unit 122 is located at a terminal end of the aerosol flow path 121, and is configured to open the aerosol flow path 121 to the outside of the aerosol generation device 100A. The user holds the mouthpiece unit 122 in the user's mouth and performs the inhalation to thereby take the air containing the aerosol in the user's mouth.

The notifying unit 108 may include a light emitting element such as an LED, a display, a speaker, a vibrator, or the like. The notifying unit 108 is configured to perform some notification to the user with light emission, display, sound production, vibration, or the like according to necessity.

The power supply 110 supplies electric power to the components such as the notifying unit 108, the sensor 112, the memory 114, the load 132, and the circuit 134 of the aerosol generation device 110A. The power supply 110 can also be charged by being connected to an external power supply via a predetermined port (not illustrated) of the aerosol generation device 100A. Only the power supply 110 may be detachable from the main body 102 or the aerosol generation device 100A, or may be replaceable with a new power supply 110. The power supply 110 may be replaceable with a new power supply 110 by replacing the entire main body 102 with a main body 102.

The sensor 112 may also include one or more sensors that are used to acquire a value of a voltage applied to all or a specific portion in the circuit 134, a value related to a resistance value of the load 132, a value related to a temperature of the load 132. The sensor 112 may be incorporated in the circuit 134, or the like. The function of the sensor 112 may be incorporated in the control unit 106. The sensor 112 may also include the pressure sensor that detects fluctuation in pressure in the air intake channel 120 and/or the aerosol flow path 121 or the flow sensor that detects a flow rate in the air intake channel 120 and/or the aerosol flow path 121. The sensor 112 may also include a weight sensor that detects a weight of a component such as the storage unit 116A. The sensor 112 may be also configured to count the number of times that the user puffs using the aerosol generation device 100A. The sensor 112 may be also configured to integrate an energization time to the atomizing unit 118A. The sensor 112 may be also configured to detect a height of a liquid surface in the storage unit 116A. The control unit 106 and the sensor 112 may be also configured to obtain or detect an SOC (State of Charge), a current integrated value, a voltage and the like of the power supply 110. The SOC may be obtained by a current integration method (coulomb counting method), an SOC-OCV (Open Circuit Voltage) method, or the like. The sensor 112 may be also an operation button or the like that is operable by the user.

The control unit 106 may be an electronic circuit module configured as a microprocessor or a microcomputer. The control unit 106 may be also configured to control the operation of the aerosol generation device 100A according to computer executable instructions stored in the memory 114. The memory 114 is a storage medium such as a ROM, a RAM, or a flash memory. In the memory 114, in addition to the above-mentioned computer executable instructions, setting data required for controlling the aerosol generation device 100A and the like may be stored. For example, the memory 114 may store various pieces of data such as a control program of the notifying unit 108 (aspects, etc. of light emission, sound production, vibration, etc.), a control program of the atomizing unit 118A, a value acquired and/or detected by the sensor 112, and a heating history of the atomizing unit 118A. The control unit 106 reads the data from the memory 114 according to necessity to use it for control of the aerosol generation device 100A, and stores the data in the memory 114 according to necessity.

Figure 1B:
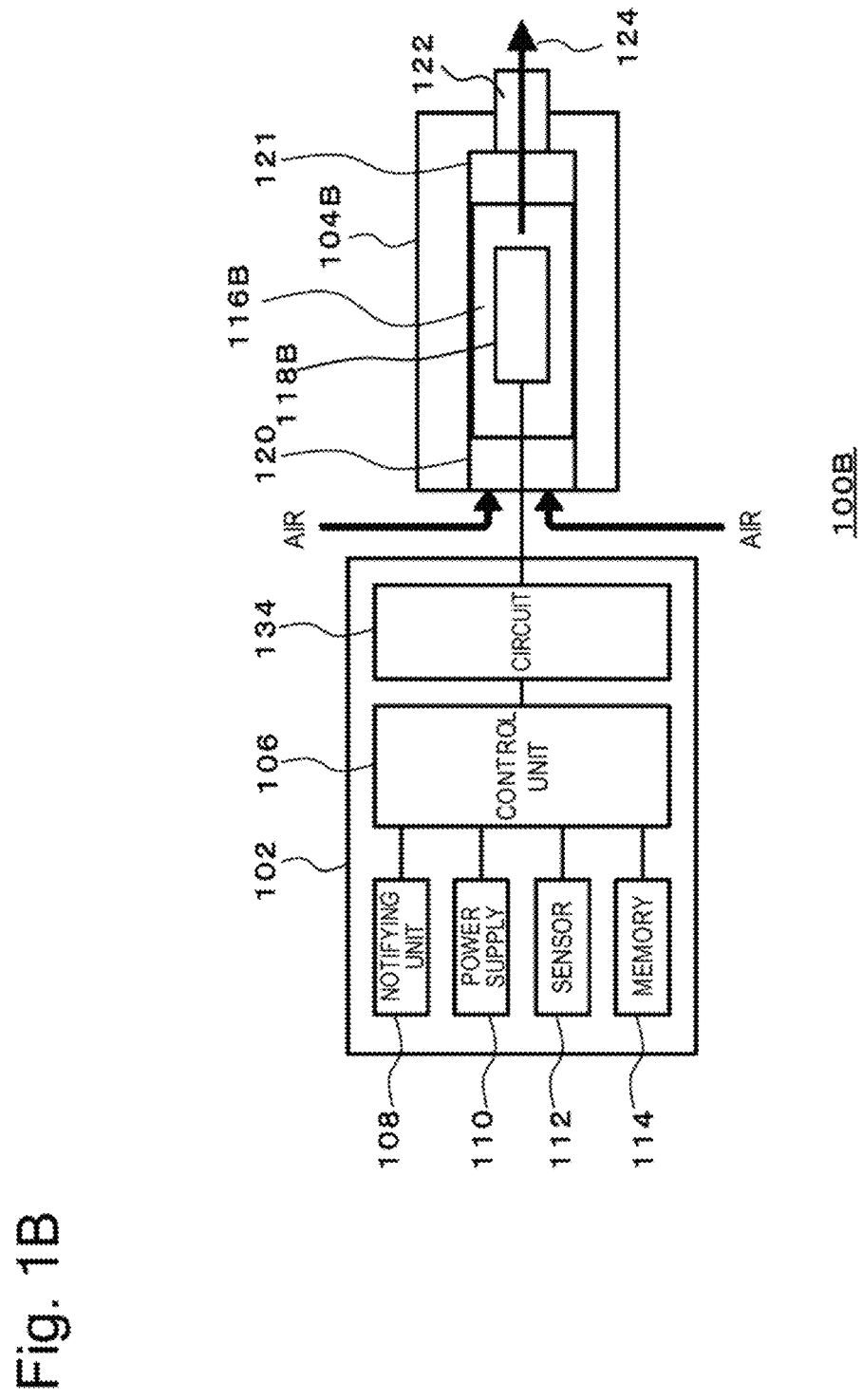
FIG. 1B is a schematic block diagram of a configuration of an aerosol generation device according to an embodiment of the present disclosure.

FIG. 1B is a schematic block diagram of a configuration of an aerosol generation device 100B according to an embodiment of the present disclosure.

As illustrated in the figure, the aerosol generation device 100B has a configuration similar to that of the aerosol generation device 100A of FIG. 1A. Note that a configuration of a second member 104B (hereinafter, referred to as an "aerosol generating article 104B" or a "stick 104B") is different from that of the first member 104A. As an example, the aerosol generating article 104B may include an aerosol base material 116B, an atomizing unit 118B, an air intake channel 120, an aerosol flow path 121, and a mouthpiece unit 122. Some of the components included in the main body 102 may be included in the aerosol generating article 104B. Some of the components included in the aerosol generating article 104B may be included in the main body 102. The aerosol generating article 104B may be configured to be insertable/extractable into/from the main body 102. Alternatively, all the components included in the main body 102 and the aerosol generating article 104B may be included in the same housing instead of the main body 102 and the aerosol generating article 104B.

The aerosol base material 116B may be configured as a solid carrying the aerosol source. As in the case of the storage unit 116A in FIG. 1A, the aerosol source may be liquid, for example, polyalcohol such as glycerin or propylene glycol, or water. The aerosol source in the aerosol base material 116B may include a tobacco raw material that emits an inhaling flavor component by being heated or an extract deriving from the tobacco raw material. When the aerosol generation device 100A is a medical inhaler such as a nebulizer, the aerosol source may also include a drug to be inhaled by a patient. The aerosol base material 116B itself may be configured to be replaceable when the aerosol source is consumed. The aerosol source is not limited to liquid, and may be a solid.

The atomizing unit 118B is configured to atomize the aerosol source and generate aerosol. When an inhaling operation is detected by the sensor 112, the atomizing unit 118B generates the aerosol. The atomizing unit 118B includes a heater (not illustrated) including a load that is electrically connected to the power supply 110. When an inhaling operation is detected, the control unit 106 controls the heater of the atomizing unit 118B or the power supply to the heater, and heats the aerosol source carried in the aerosol base material 116B to thereby atomize the aerosol source. Another example of the atomizing unit 118B may be an ultrasonic atomizer that atomizes the aerosol source by ultrasonic vibration. The air intake channel 120 is connected to the atomizing unit 118B, and communicates with the outside of the aerosol generation device 100B. The aerosol generated in the atomizing unit 118B is mixed with air taken in via the air intake channel 120. Mixed fluid of the aerosol and the air is delivered to the aerosol flow path 121 as indicated by an arrow 124. The aerosol flow path 121 has a tubular structure for transporting, to the mouthpiece unit 122, the mixed fluid of the aerosol generated in the atomizing unit 118B and the air. Note that in the aerosol generation device 100B, the aerosol generating article 104B is configured to be heated from the inside by the atomizing unit 118B that is located in the aerosol generating article 104B or is inserted into the inside of the aerosol generating article 104B. Alternatively, the aerosol generating article 104B may be also configured to be heated from the outside by the atomizing unit 118B configured to surround or accommodate the aerosol generating article 104B.

The control unit 106 is configured to control the aerosol generation devices 100A and 100B (hereinafter also generically referred to as an "aerosol generation device 100") according to the embodiment of the present disclosure in various methods.

In the aerosol generation device, if the user performs the inhalation when the aerosol source is insufficient in quantity, a sufficient quantity of aerosol cannot be supplied to the user. In addition, in the case of the electronic cigarette or the heated cigarette, the aerosol having an unintended inhaling flavor may be emitted (hereinafter, such a phenomenon is also referred to as "unintended behavior"). The unintended behavior may occur not only when the aerosol source in the storage unit 116A or the aerosol base material 116B is insufficient in quantity, but also when a sufficient quantity of aerosol source remains in the storage unit 116A but the aerosol source in the retention unit 130 is temporarily insufficient in quantity. The present inventors have invented an aerosol generation device that performs an appropriate control when an aerosol source is insufficient in quantity, and a method and a program for actuating the same. Hereinafter, each embodiment of the present disclosure will be described in detail, while mainly assuming the case where the aerosol generation device has a configuration illustrated in FIG. 1A. However, the case where the aerosol generation device has a configuration illustrated in FIG. 1B is also described according to necessity. It will be apparent to those skilled in the art that the embodiment of the present disclosure is also applicable to the case where the aerosol generation device has various configurations other than those illustrated in FIG. 1A and FIG. 1B.

First Embodiment

Figure 2:
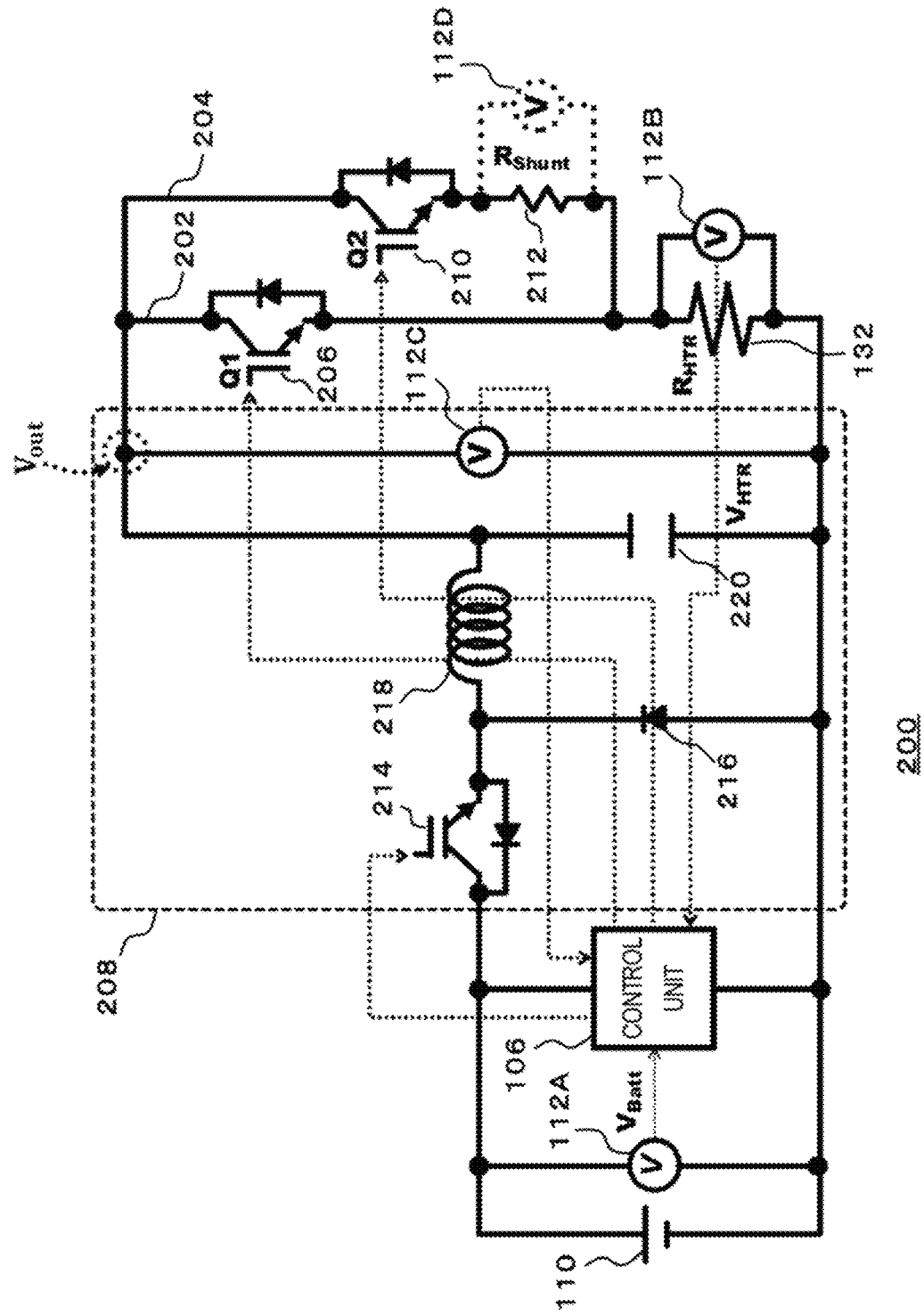
FIG. 2 is a diagram illustrating an exemplary circuit configuration of a portion of an aerosol generation device according to an embodiment of the present disclosure.

FIG. 2 is a diagram illustrating an exemplary circuit configuration of a portion of the aerosol generation device 100A according to a first embodiment of the present disclosure. A circuit 200 illustrated in FIG. 2 includes the power supply 110, the control unit 106, the sensors 112A to 112D (hereinafter also collectively referred to as the "sensor 112"), the load 132 (hereinafter also referred to as a "heater resistor"), a first circuit 202, a second circuit 204, a switch Q1 including a first field emission transistor (FET) 206, a conversion unit 208, a switch Q2 including a second FET 210, and a resistor 212 (hereinafter, also referred to as a "shunt resistor"). Note that the sensor 112 may be embedded in the other component such as the control unit 106 or the conversion unit 208. The electric resistance value of the load 132 changes in response to the temperature by using, for example, a positive temperature coefficient (PTC) heater or a negative temperature coefficient (NTC) heater. The shunt resistor 212 is connected in series with the load 132, and has a known electric resistance value. The electric resistance value of the shunt resistor 212 may be substantially invariant to the temperature. The shunt resistor 212 has an electric resistance value larger than that of the load 132. Depending on the embodiment, the sensors 112C and 112D may be omitted. It will be apparent to those skilled in the art that not only FET but also various elements such as iGBT and a contactor can be used as the switches Q1 and Q2.

The conversion unit 208 may be, for example, a switching converter, and may include a FET 214, a diode 216, an inductance 218, and a capacitor 220. The control unit 106 may control the conversion unit 208 so that the conversion unit 208 converts an output voltage of the power supply 110 to apply the converted output voltage to the entire circuit. Instead of a step-down type switching converter illustrated in FIG. 2, a step-up type switching converter, a step-up/step-down type switching converter, a linear dropout (LDO) regulator, or the like may be used. Note that the conversion unit 208 is not an essential component, and can be omitted. Furthermore, a control unit (not illustrated) provided separately from the control unit 106 may be configured to control the conversion unit 208. This not-illustrated control unit may be embedded in the conversion unit 208.

The circuit 134 illustrated in FIG. 1A may be electrically connected to the power supply 110 and the load 132, and may include the first circuit 202 and the second circuit 204. The first circuit 202 and the second circuit 204 are connected in parallel to the power supply 110 and the load 132. The first circuit 202 may include the switch Q1. The second circuit 204 may include the switch Q2 and the resistor 212 (and optionally the sensor 112D). The first circuit 202 may have a resistance value smaller than that of the second circuit 204. In this example, the sensors 112B and 112D are voltage sensors, and are configured to detect a voltage value across the load 132 and a voltage value across the resistor 212, respectively. However, a configuration of the sensor 112 is not limited thereto. For example, the sensor 112 may be a current sensor using a known resistor or a hall element, and may detect a value of a current flowing through the load 132 and/or the resistor 212.

As indicated by dotted-line arrows in FIG. 2, the control unit 106 can control the switch Q1, the switch Q2, and the like, and can acquire a value detected by the sensor 112. The control unit 106 may be configured to switch the switch Q1 from an off state to an on state to cause the first circuit 202 to function and configured to switch the switch Q2 from the off state to the on state to cause the second circuit 204 to function. The control unit 106 may be configured to alternately switch the switches Q1 and Q2 to alternately cause the first circuit 202 and the second circuit 204 to function.

The first circuit 202 is used to atomize the aerosol source. When the switch Q1 is switched to the on state to cause the first circuit 202 to function, the electric power is supplied to the heater (or the load 132 in the heater), and the load 132 is heated. The aerosol source retained in the retention unit 130 in the atomizing unit 118A (in the case of the aerosol generation device 100B of FIG. 1B, the aerosol source carried in the aerosol base material 116B) is atomized through heating by the load 132, whereby the aerosol is generated.

The second circuit 204 is used to acquire a value of a voltage applied to the load 132, a value related to a resistance value of the load 132, a value of a voltage applied to the resistor 212, and the like. As an example, it is assumed that the sensors 112B and 112D are voltage sensors as illustrated in FIG. 2. When the switch Q2 is on and the second circuit 204 is functioning, the current flows through the switch Q2, the resistor 212, and the load 132. A value of the voltage applied to the load 132 and/or a value of the voltage applied to the resistor 212 can be obtained by the sensors 112B and 112D. In addition, a value of a current flowing the load 132 can be obtained using the value of the voltage applied to the resistor 212 that has been acquired by the sensor 112D and a known resistance value $R_{shunt}$ of the resistor 212. Since a total value of the resistance values of the resistor 212 and the load 132 can be obtained based on an output voltage $V_{out}$ of the conversion unit 208 and the obtained current value, a resistance value $R_{HTR}$ of the load 132 can be obtained by subtracting the known resistance value $R_{shunt}$ from the total value. When the load 132 has a positive or negative temperature coefficient characteristic in which the resistance value changes in response to the temperature, the temperature of the load 132 can be estimated based on a relationship between the pre-known resistance value of the load 132 and the temperature of the load 132, and the resistance value $R_{HTR}$ of the load 132 that is obtained as described above. It will be appreciated by those skilled in the art that the resistance value and the temperature of the load 132 can be estimated using a value of the current flowing through the resistor 212. The value related to the resistance value of the load 132 in this example may include a voltage value, a current value and the like of the load 132. A specific example of the sensors 112B and 112D is not limited to the voltage sensor, and may include the other elements such as a current sensor (for example, a hall element).

The sensor 112A detects an output voltage during discharging or in a no-load state of the power supply 110. The sensor 112C detects an output voltage of the conversion unit 208. Alternatively, the output voltage of the conversion unit 208 may be a predetermined target voltage. These voltages are voltages applied to the entire circuit.

The resistance value $R_{HTR}$ of the load 132 when the temperature of the load 132 is "$T_{HTR}$" can be expressed as follows.

$$R_{HTR}(T_{HTR})=(V_{HTR} \times R_{shunt})/(V_{Batt}-V_{HTR})$$

Where $V_{Batt}$ is a voltage applied to the entire circuit. When the conversion unit 208 is not used, "$V_{Batt}$" is an output voltage of the power supply 110. When the conversion unit 208 is used, "$V_{Batt}$" corresponds to the target voltage of the conversion unit 208. "$V_{HTR}$" is a voltage applied to the heater. Instead of "$V_{HTR}$," the voltage applied to the shunt resistor 212 may be used.

As described below, according to the present embodiment, the control unit 106 can determine whether the aerosol source that can be supplied from the storage unit 116A (or the aerosol source carried in the aerosol base material 116B) is insufficient in quantity based on a value (hereinafter also referred to as a "first voltage value") of a voltage (an output voltage of the power supply 110 or a target voltage of the conversion unit 208) applied to the entire circuit and a value (hereinafter also referred to as a "second voltage value") of a voltage (a voltage applied to the load 132 or the shunt resistor 212) applied to a portion in the circuit where the voltage to be applied changes according to changes in temperature of the load 132. According to the present embodiment, it becomes possible to determine whether the aerosol source is insufficient in quantity only by adding a minimal sensor to the configuration of the conventional aerosol generation device. In particular, when the conversion unit 208 is used, a parameter to be acquired from the sensor 112 in the above-described expression for obtaining the resistance value $R_{HTR}$ of the load 132 is only a voltage applied to the heater or a voltage applied to the shunt resistor 212, and therefore it is only necessary to store other values as constants in the memory 114. Accordingly, the influence of errors of the sensor 112 on the resistance value $R_{HTR}$ of the load 132 can be reduced to minimum, thereby significantly improving the accuracy of determining whether the unintended behavior has occurred.

Figure 3:
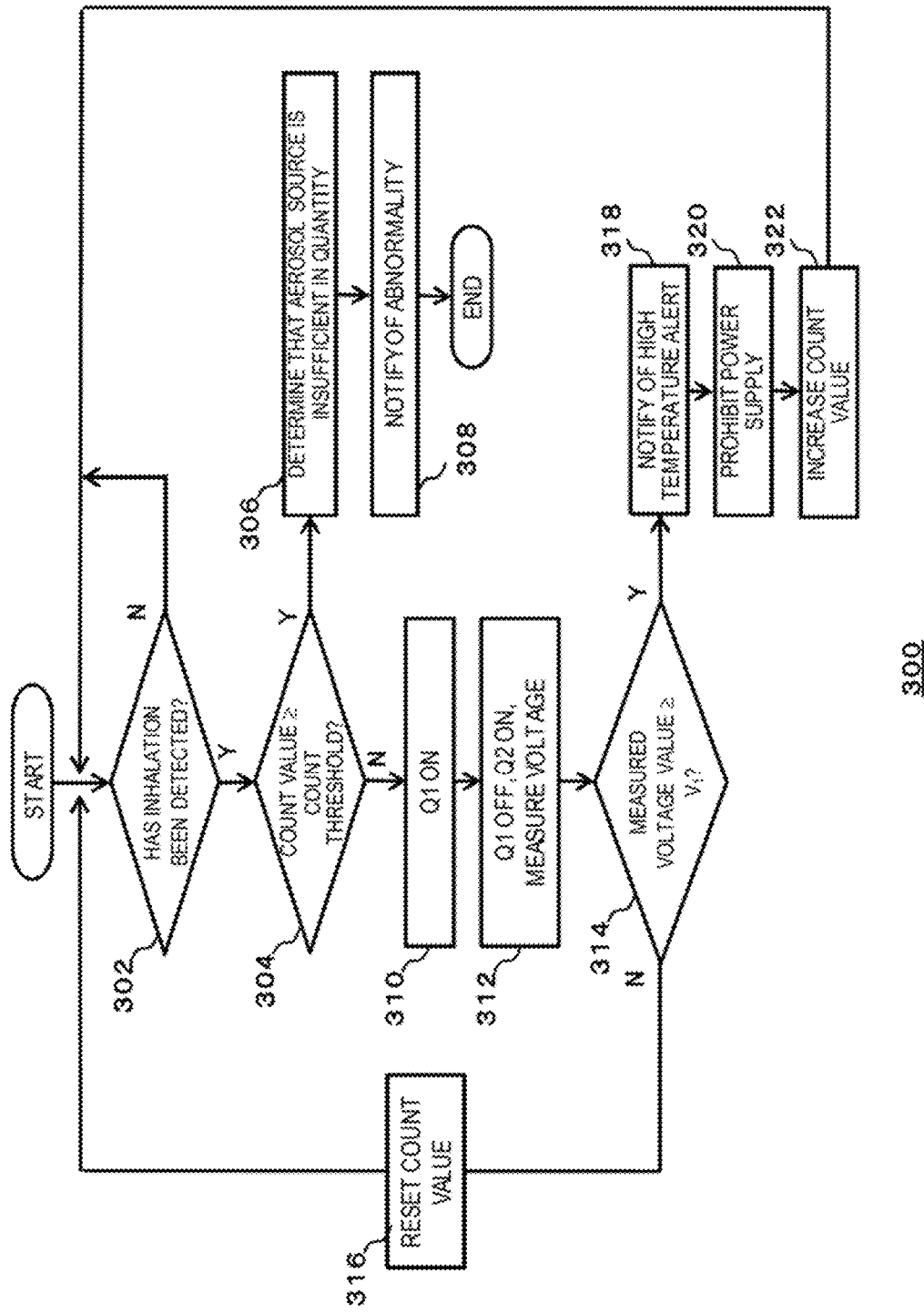
FIG. 3 is a flowchart of exemplary processing of determining whether an aerosol source is insufficient in quantity, according to an embodiment of the present disclosure.

FIG. 3 is a flowchart of exemplary processing of determining whether the aerosol source is insufficient in quantity, according to an embodiment of the present disclosure. Here, all the steps will be described as being performed by the control unit 106. However, it should be noted that some of the steps may be performed by another component in the aerosol generation device 100.

The process starts at step 302. In step 302, the control unit 106 determines whether the user's inhalation has been detected, based on the information obtained from the pressure sensor, the flow sensor, and the like. For example, when the output values of these sensors continuously change, the control unit 106 may determine that the user's inhalation has been detected. Alternatively, the control unit 106 may determine that the user's inhalation has been detected, based on a fact that a button for starting the generation of the aerosol has been pressed, etc.

When the inhalation is not detected ("N" in step 302), the process of step 302 is repeated.

When it is determined that the inhalation has been detected ("Y" in step 302), the process proceeds to step 304. In step 304, the control unit 106 determines whether a present count value is equal to or greater than a predetermined count threshold (for example, 3). Here, the count value indicates the number of times that a first condition (or a second condition) detected in step 314 described later is satisfied. The count value may be stored in the memory 114.

When the count value is equal to or greater than the count threshold ("Y" in step 304), the process proceeds to step 306. In step 306, the control unit 106 determines that the aerosol source that can be supplied from the storage unit 116A (or the aerosol source carried in the aerosol base material 116B) is insufficient in quantity. The process proceeds to step 308, and the control unit 106 performs a control to notify the user of the abnormality (insufficiency of the aerosol source). For example, the control unit 106 may cause the notifying unit 108 to perform the operation such as light emission, display, sound production, or vibration to notify the user of the abnormality. After step 308, the process ends. In this case, in order to generate the aerosol again using the aerosol generation device 100, it is necessary to replace the cartridge 104A or the aerosol generating article 104B, to refill the storage unit 116A or the aerosol base material 116B with the aerosol source, or the like.

When the count value is lower than the count threshold ("N" in step 304), the process proceeds to step 310. In step 310, the control unit 106 switches the switch Q1 to the on state, and causes the first circuit 202 to function. As a result, the electric power is supplied to the load 132, and the aerosol source is atomized, whereby the aerosol is generated.

The process proceeds to step 312. The control unit 106 switches the switch Q1 to the off state, and switches the switch Q2 to the on state. Accordingly, the second circuit 204 functions. The control unit 106 measures, using the sensor 112B, a value of the voltage applied to the load 132. Alternatively, the control unit 106 may measure, using the sensor 112D, a value of the voltage applied to the shunt resistor 212. Since the electric resistance value of the load 132 changes in response to the temperature, the voltage applied to the load 132 and the voltage applied to the shunt resistor 212 change when the temperature of the load 132 changes.

The process proceeds to step 314, and the control unit 106 compares the voltage value measured in step 312 with a predetermined threshold (for example, $V_1$), and determines whether the measured voltage value is equal to or higher than "$V_1$". Here, when the temperature of the load 132 becomes a predetermined temperature which is higher than a boiling point of the aerosol source, "$V_1$" can be a voltage value applied to the load 132. Note that the voltage $V_{HTR}$ applied to the load 132 when the temperature of the load 132 is "$T_{HTR}$" can be expressed as follows.

$$V_{HTR}(T_{HTR}) = I_{HTR}(T_{HTR}) \times R_{HTR}(T_{HTR})$$

Here, "$I_{HTR}(T_{HTR})$" is a current flowing through the load 132 when the temperature of the load 132 is "$T_{HTR}$". The expression can be modified as follows.

$$V_{HTR}(T_{HTR}) = V_{Batt} / \{R_{shunt} + R_{HTR}(T_{HTR})\} \times R_{HTR}(T_{HTR})$$
$$= R_{HTR} / \{R_{shunt} + R_{HTR}(T_{HTR})\} \times V_{Batt}$$
$$= 1 / \{R_{shunt} / R_{HTR}(T_{HTR}) + 1\} \times V_{Batt}$$

Accordingly, when the temperature of the load 132 rises, the voltage applied to the load 132 increases.

Alternatively, instead of the voltage applied to the load 132, the control unit may compare the voltage applied to the shunt resistor 212 with the predetermined threshold, in step 314. It should be noted that in order to compare the voltage applied to the shunt resistor 212 with the predetermined threshold, it is necessary to determine whether the voltage applied to the shunt resistor 212 is equal to or lower than the predetermined threshold. This can be described as follows. Firstly, the voltage $V_{shunt}$ applied to the shunt resistor 212 when the temperature of the load 132 is "$T_{HTR}$" can be expressed as follows.

$$V_{shunt}(T_{HTR}) = V_{Batt} - V_{HTR}(T_{HTR})$$

When the voltage $V_{HTR}$ applied to the load 132 when the temperature of the above-described load 132 is "$T_{HTR}$" is substituted into this expression, this expression can be modified as follows.

$$V_{shunt}(T_{HTR}) = V_{Batt} - 1/\{R_{shunt} / R_{HTR}(T_{HTR}) + 1\} \times V_{Batt}$$
$$= [1 - 1/\{R_{shunt} / R_{HTR}(T_{HTR}) + 1\}] \times V_{Batt}$$

Accordingly, when the temperature of the load 132 rises, the voltage applied to the load 132 decreases. That is, in order to determine whether the notice for a high temperature alert in subsequent step 318 and the power supply to the load 132 in subsequent step 320 are prohibited or stopped, it is necessary to determine whether the voltage applied to the shunt resistor 212 is equal to or lower than the predetermined threshold.

In step 314, the control unit 106 may determine whether the second voltage value (a value of the voltage applied to the load 132 or a value of the voltage applied to the shunt resistor 212) satisfies the first condition while the first voltage value (a value of the voltage applied to the entire circuit) is controlled to be constant. Note that as described above, when a value of the voltage applied to the load 132 is used for the second voltage value, the first condition is whether the second voltage value is equal to or higher than "$V_1$," and when a value of the voltage applied to the shunt resistor 212 is used for the second voltage value, the first condition is whether the second voltage value is equal to or lower than "$V_1$". Alternatively, the control unit 106 may determine whether the electric resistance value of the load 132 derived from the first voltage value and the second voltage value satisfies the second condition (electric resistance value is equal to or higher than the predetermined resistance value $R_1$). In the case where the first condition or the second condition is satisfied a plurality of times, after step 304, the process proceeds to step 306, and it may be determined that the aerosol source is insufficient in quantity. According to this configuration, in the case where the predetermined condition is satisfied a plurality of times, it is determined that the aerosol source is insufficient in quantity. The aerosol source is not necessarily insufficient in quantity, even when the predetermined condition is satisfied due to such factors as a noise contained in the output value of the sensor 112, a resolution of the sensor 112, and dryness in at least part of the retention unit 130 or the aerosol base material 116B that is caused by the inhalation method although a sufficient quantity of aerosol source remains in the storage unit 116A or the entire aerosol base material 116B. Accordingly, the detection accuracy with respect to the insufficiency of the aerosol source is more improved as compared with the case where it is determined that the aerosol source is insufficient in quantity when the condition is satisfied only once.

When the conversion unit 208 (the switching converter or the like) illustrated in FIG. 2 is used, the control unit 106 controls the conversion unit 208 so that the conversion unit 208 converts an output voltage of the power supply 110 to apply the converted output voltage to the entire circuit. The control unit 106 controls the conversion unit 208 to output a constant voltage. This enables the first voltage to be stabilized, and the detection accuracy as to whether the aerosol source is insufficient in quantity is more improved as compared with the case where the voltage itself of the power supply 110 is applied. In this case, the first condition may be determined in step 314. That is, it may be determined whether the aerosol source is insufficient in quantity, using only the second voltage value. On the other hand, when the conversion unit 208 is not used, the second condition may be determined in step 314.

In this example, the control unit 106 determines whether the aerosol source is insufficient in quantity, based on the first voltage value which is a value of the above-described constant voltage and the second voltage value which is output from the sensor 112B or 112D. The control unit 106 may determine whether the aerosol source is insufficient in quantity based on comparison between the second voltage value output from the sensor 112B or 112D and the predetermined threshold. In this case, it is only required that only the second voltage is detected, whereby there is less room for noise to be introduced, and the detection accuracy is improved.

The sensor 112B may be configured to output the second voltage value based on comparison between a reference voltage and an amplified voltage applied to the load 132. For example, the sensor 112B may obtain a difference (an analog value) between the reference voltage that is an analog value and an amplified value of the voltage applied to the load 132 which is an analog value, and convert the difference into a digital value. The digital value may be used as the above-described second voltage value.

In an example, the first voltage value may be stored in the memory 114. The control unit 106 may acquire the first voltage value and the second voltage value from the memory 114 and the sensor 112B or 112D, respectively.

When the conversion unit 208 is not used, the first voltage value and the second voltage value are output using the sensor 112A, and the sensor 112B or the sensor 112D, respectively. The control unit 106 may determine whether the aerosol source is insufficient in quantity based on comparison between the electric resistance value of the load 132 derived from the output values obtained from these sensors and the predetermined threshold.

When the measured voltage value is lower than "$V_1$" ("N" in step 314), the process proceeds to step 316. In step 316, the control unit 106 may reset the count value. For example, the control unit 106 may return the count value to an initial value.

Thus, in the processing 300, the control unit 106 may return the count value to the initial value (for example, zero) when the first condition is not satisfied or the second condition is not satisfied. In this manner, even when the condition is satisfied only once due to temporary dryness of the retention unit 130 or the like, the detection accuracy can be secured thereafter.

When the measured voltage value is equal to or higher than "$V_1$" ("Y" in step 314), the process proceeds to step 318. In this case, the temperature of the load 132 becomes higher than necessary. In step 318, the control unit 106 notifies of a high temperature alert. For example, the control unit 106 may cause the notifying unit 108 to operate in a predetermined manner to thereby notify of the alert.

The process proceeds to step 320, and the control unit 106 prohibits or stops the power supply to the load 132. Next, in step 322, the control unit 106 increases the count value. For example, the control unit 106 increases the counter value by 1. After step 322, the process returns to before step 302. Note that steps 318 and 320 may be omitted.

In the processing 300, when the above-described first condition is continuously satisfied a plurality of times or the above-described second condition is continuously satisfied a plurality of times, the control unit 106 may determine that the aerosol source is insufficient in quantity. This will still further improve the detection accuracy with respect to the insufficiency of the aerosol source. Note that after step 322, the determination in step 304 may be performed without waiting for detection of the user's inhalation in step 302.

According to the embodiment in FIG. 3, the control unit 106 can determine whether the aerosol source that can be supplied from the storage unit 116A or the aerosol source retained in the aerosol base material 116B is insufficient in quantity based on the first voltage value which is a value of the voltage applied to the entire circuit and the second voltage value which is a value of the voltage applied to a portion in the circuit where the voltage to be applied changes according to changes in temperature of the load 132. That is, it is possible to estimate a residual quantity of the aerosol source that can be supplied from the storage unit 116A or the aerosol source retained in the aerosol base material 116B.

Figure 4:
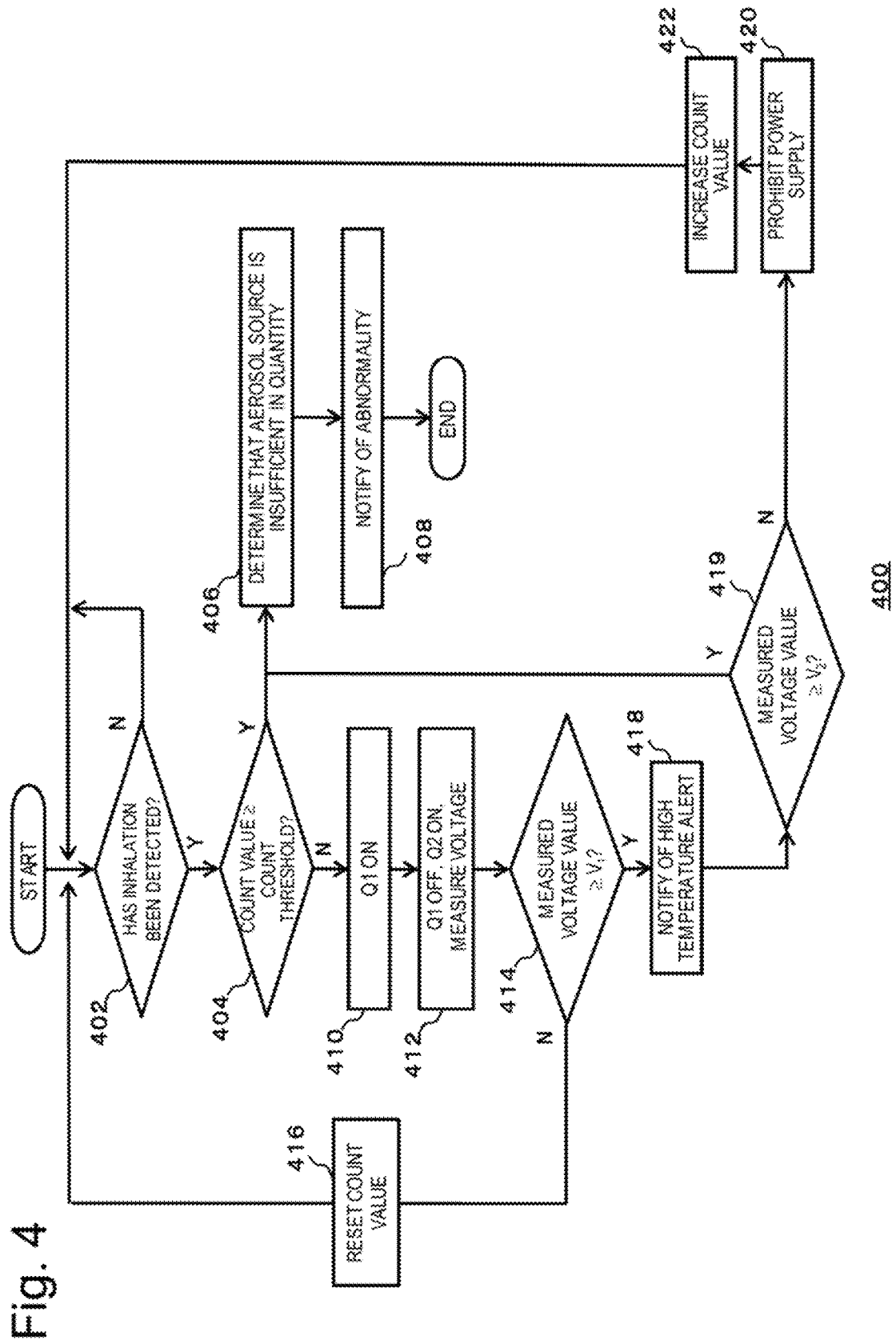
FIG. 4 is a flowchart of exemplary processing of determining whether the aerosol source is insufficient in quantity, according to an embodiment of the present disclosure.

FIG. 4 is a flowchart of exemplary processing of determining whether the aerosol source is insufficient in quantity, according to another embodiment of the present disclosure.

The processes in steps 402 to 418 in FIG. 4 are the same as the processes in steps 302 to 318 in FIG. 3. Here, description thereof is omitted.

After step 418, the process proceeds to step 419. In step 419, the control unit 106 determines whether the voltage value applied to the load 132 that is measured in step 412 is equal to or higher than a predetermined threshold ($V_2$). "$V_2$" may be a voltage value applied to the load 132 when the temperature of the load 132 becomes a predetermined temperature further higher than "$V_1$". It should be noted that, as described above, when instead of the voltage value applied to the load 132, the voltage value applied to the shunt resistor 212 is used, "$V_2$" is a value smaller than "$V_1$," and the control unit 106 determines whether the voltage value applied to the shunt resistor 212 is equal to or lower than "$V_2$".

When the measured voltage value is equal to or higher than "$V_2$" ("Y" in step 419), the process proceeds to steps 406 and 408, and then the process ends.

When the measured voltage value is lower than "$V_2$" ("N" in step 419), the process proceeds to step 420. The processes in steps 420 and 422 are the same as the processes in steps 320 and 322, and description thereof is omitted. Note that after step 422, the determination in step 404 may be performed without waiting for detection of the user's inhalation in step 402.

Thus, in the processing 400, the control unit 106 determines whether the aerosol source is insufficient in quantity using a first reference based on the first voltage value and the second voltage value (step 414) and a second reference different from the first reference (step 419). When the first reference is satisfied a plurality of times or the second reference is satisfied a smaller number of times than the plurality of times, the control unit 106 determines that the aerosol source is insufficient in quantity. It is more difficult to satisfy the second reference than the first reference. In this manner, the processing 400 has two-stage determination criterion, thereby enabling immediate determination whether the aerosol is insufficient in quantity and improving the quality of the aerosol generation device 100.

In an example, when the voltage value applied to the load 132 is used as the second voltage value, the first reference may be whether the second voltage value satisfies the first threshold (for example, the second voltage value is equal to or higher than "$V_1$") while the first voltage value is controlled to be constant, or whether the electric resistance value of the load 132 derived from the first voltage value and the second voltage value satisfies the second threshold (for example, the electric resistance value is equal to or higher than the predetermined threshold $R_1$). When the voltage value applied to the load 132 is used as the second voltage value, the second reference may be whether the second voltage value satisfies a threshold greater than the first threshold or whether the electric resistance value of the load 132 satisfies the threshold greater than the second threshold.

In an example, when the voltage value applied to the shunt resistor 212 is used as the second voltage value, the first reference may be whether the second voltage value satisfies the first threshold (for example, the second voltage value is equal to or lower than "$V_1$") while the first voltage value is controlled to be constant, or whether the electric resistance value of the load 132 derived from the first voltage value and the second voltage value satisfies the second threshold (for example, the electric resistance value is equal to or higher than the predetermined threshold $R_1$). When the voltage value applied to the shunt resistor 212 is used as the second voltage value, the second reference may be whether the second voltage value satisfies a threshold smaller than the first threshold or whether the electric resistance value of the load 132 satisfies the threshold greater than the second threshold.

As a variant of the processing 400 of FIG. 4, step 419 may be performed earlier than step 414. That is, the control unit 106 may be configured to determine whether the second reference is satisfied before determining whether the first reference is satisfied.

In an example, when the second reference is satisfied and it is determined that the aerosol source is insufficient in quantity, the control unit 106 may perform at least one of stop of supply of the electric power from the power supply 110 to the load 132 or the notification to the user without determining whether the first reference is satisfied.

FIG. 5 is a flowchart of exemplary processing of determining whether the aerosol source is insufficient in quantity, according to another embodiment of the present disclosure.

The processes in steps 502 to 514 and 518 to 522 in FIG. 5 are the same as the processes in steps 302 to 314 and 318 to 322 in FIG. 3, and description thereof is omitted.

In step 514, when the measured voltage value which is a voltage value applied to the load 132 is lower than "$V_1$" ("N" in step 514), the process proceeds to step 516. In step 516, the control unit 106 does not reset the count value but decreases the count value. For example, when the count value before the process in step 516 is 2, the control unit 106 may set the count value to 1 by decreasing the count value by 1. It should be noted that in the case where the voltage value applied to the shunt resistor 212 is used as the measured voltage value, when the measured voltage value exceeds "$V_1$" ("N" in step 514), the process proceeds to step 516.

Thus, in the processing 500, the control unit may store the number of times that the first condition is satisfied or the number of times that the second condition is satisfied, and decrease the number of times when the first condition is not satisfied or the second condition is not satisfied. In this manner, even when the condition is satisfied only once due to temporary dryness of the retention unit 130 or the like, the detection accuracy can be secured thereafter.

In an example, the aerosol generation device 100 may include a connecter that allows the attachment/detachment of the cartridge 104A including the storage unit 116A or the aerosol generating article 104B including the aerosol base material 116B and that allows detection of the attachment/detachment of the cartridge 104A or the aerosol generating article 104B. For example, the aerosol generation device 100 may include a physical switch used for the above-described attachment and detachment, a magnetic detection unit that detects the attachment or detachment, and the like. The control unit 106 may have a function of authenticating ID of the cartridge 104A or the aerosol generating article 104B. The control unit 106 may detect the attachment or detachment of the cartridge 104A or the aerosol generating article 104B based on the fact that the physical switch has been actuated, the magnetic detection unit has detected a change in the magnetic field, the ID of the cartridge 104A or the aerosol generating article 104B to be attached has changed, or the like. The control unit 106 may be configured to store the number of times that the first condition is satisfied or the number of times that the second condition is satisfied and to decrease the number of times when the cartridge 104A or the aerosol generating article 104B is attached to the connecter. In this example, when the cartridge 104A or the aerosol generating article 104B is replaced, the count value is decreased. Accordingly, it is not necessary to inherit the count value stored for the cartridge 104A or the aerosol generating article 104B before replacement, whereby the detection accuracy for the new cartridge 104A or new aerosol generating article 104B is improved.

In the above-described example, it may be possible to acquire the identification information or the usage history of the cartridge 104A or the aerosol generating article 104B in a predetermined manner. The control unit 106 may determine whether to decrease the above-described number of times based on the identification information or the usage history of the cartridge 104A or the aerosol generating article 104B that is attached to the connecter. For example, when the cartridge 104A or the aerosol generating article 104B is replaced with a new one, the count value may be decreased. Accordingly, if the same cartridge 104A or aerosol generating article 104B is connected again, the number of times is not reset, whereby the detection accuracy for this cartridge is improved.

FIG. 6 is a flowchart of exemplary processing performed when a user's inhalation pattern is an unexpected pattern, according to an embodiment of the present disclosure. The processing in FIG. 6 may be performed at any appropriate stage in the processing of the embodiments of the present disclosure which are described in FIG. 3 to FIG. 5.

In step 602, the control unit 106 measures a user's inhalation pattern using the flow sensor, the pressure sensor, or the like.

The process proceeds to step 604, and the control unit 106 determines whether the measured inhalation pattern is an unexpected inhalation pattern. For example, the control unit 106 may perform the determination by comparing the measured inhalation pattern with a normal inhalation pattern stored in the memory 114. The normal inhalation pattern may include various patterns known to those skilled in the art, including gaussian distribution and the like. The control unit 106 may perform the determination of step 604 based on whether a height and a skirt length of the measured inhalation pattern, an interval between the inhalation and the next inhalation, and the like are deviated from the normal values in the normal inhalation pattern by a predetermined threshold.

When the measured inhalation pattern is an unexpected inhalation pattern ("Y" in step 604), the process proceeds to step 606. In step 606, the control unit 106 may increase the count thresholds used in steps 304, 404, and 504. Alternatively, the control unit 106 may change the contents of processing so that the count value is not increased in steps 322, 422, and 522. Alternatively, the control unit 106 may reduce the increase amount of the count values used in steps 322, 422, and 522.

When measured inhalation pattern is not an unexpected inhalation pattern ("N" in step 604), the process proceeds to step 608. In step 608, the control unit 106 does not perform a setting change as performed in step 606.

Thus, in the present embodiment, when the first condition or the second condition is satisfied in a state in which a time-series change of a demand for generation of aerosol does not meet a predetermined normal change, the control unit 106 may increase the predetermined threshold (count threshold), may not increase the number of times (count value), may reduce the increase amount of the number of times (count value), or the like. In this way, even when the first condition or the second condition is satisfied when the user's inhalation is irregular such as in the case where a single inhalation is performed for a long period of time, the case where the interval between inhalations is short, or the like, the detection accuracy as to whether the aerosol source is insufficient in quantity is improved.

In the above description, the first embodiment of the present disclosure has been described as an aerosol generation device and a method of actuating the aerosol generation device. However, it will be appreciated that the present disclosure, when being executed by a processor, can be implemented as a program that causes the processor to perform the method or as a computer readable storage medium storing the same program.

Second Embodiment

As described in relation to the first embodiment of the present disclosure, the aerosol generation device 100 having configurations illustrated in FIG. 1A to FIG. 2 is actuated according to the processing illustrated in FIG. 3 to FIG. 6, whereby it is possible to determine whether the aerosol source is insufficient in quantity (to estimate the residual quantity of the aerosol source).

The state in which the aerosol source is insufficient in quantity includes the state in which the aerosol source stored in the storage unit 116A is depleted, the state in which the aerosol source retained in the retention unit 130 is temporarily depleted, and the state in which the aerosol source retained in the aerosol generating article 104B (stick 104B) is depleted and the aerosol base material 116B is dried.

The aerosol generation device 100 according to the first embodiment of the present disclosure has the small number of required components, and has high detection accuracy with respect to insufficiency of the aerosol source, and therefore is superior to that of the conventional technique. However, the sensor 112B for measuring the voltage applied to the load 132 has a product error. The sensor 112A for measuring the output voltage of the power supply 110 also has a product error. Furthermore, the output voltage of the power supply 110 in a non-equilibrium state (polarization state) tends to fluctuate. The present inventors have recognized, as a further problem to be solved, a fact that these product errors have an influence on the detection accuracy of the aerosol generation device 100 of the present disclosure. An object of the second embodiment of the present disclosure is to provide an aerosol generation device that solves this further problem, thereby further improving the detection accuracy as to whether the aerosol source is insufficient in quantity.

A basic configuration of the aerosol generation device 100 according to the present embodiment is similar to a configuration of the aerosol generation device 100 illustrated in each of FIG. 1A and FIG. 1B and a configuration of the circuit 200 illustrated in FIG. 2.

The aerosol generation device 100 includes the power supply 110, the load 132 that generates heat upon receipt of electric power from the power supply 110 and atomizes an aerosol source using the heat, and in which an electric resistance value changes in response to a temperature, the first circuit 202 used to cause the load 132 to atomize the aerosol source, the second circuit 204 used to detect the voltage that changes according to changes in temperature of the load 132, connected to the first circuit 202 in parallel, and having the electric resistance value higher than that of the first circuit 202, an acquisition unit that acquires a value of a voltage applied to the second circuit 204 and the load 132, and the sensor 112B or 112D that outputs a value of the voltage that changes according to the changes in temperature of the load 132. The aerosol generation device 100 may or may not include the conversion unit 208 such as a switching converter.

The resistance value of the load (heater) 132 can be expressed with the following expression.

$$R_{HTR}(T_{HTR}) = (V_{HTR} \times R_{shunt}) / (V_{Batt} - V_{HTR})$$
$$= (V_{Batt} - V_{shunt}) \times R_{shunt} / V_{shunt}$$

Where "$R_{HTR}$" is an electric resistance value of the load 132, "$T_{HTR}$" is a temperature of the load 132, "$V_{HTR}$" is a value of the voltage applied to the load 132, "$R_{shunt}$" is an electric resistance value of the shunt resistor 212, "$V_{Batt}$" is an output voltage of the power supply 110, and "$V_{shunt}$" is a value of the voltage applied to the shunt resistor 212. When the aerosol generation device 100 includes the conversion unit 208, "$V_{Batt}$" is an output voltage of the conversion unit 208. Since the electric resistance value of the load 132 changes in response to the changes in temperature of the load 132, the value of the voltage applied to the load 132 also changes in response to the changes in temperature of the load 132. Accordingly, the value of the voltage applied to the shunt resistor 212 also changes in response to the changes in temperature of the load 132.

When the aerosol generation device 100 does not include the conversion unit 208, the above-described acquisition unit may be the sensor 112A that detects an output voltage of the power supply 110. When the aerosol generation device 100 includes the conversion unit 208, a set value of the output voltage of the conversion unit 208 which is controlled to be constant may be stored in the memory 114. In this case, the acquisition unit may be a reader that reads the set value from the memory 114.

The second circuit 204 includes the shunt resistor 212, and the shunt resistor 212 has a known electric resistance value. The shunt resistor 212 is connected to the load 132 in series. The sensors 112B and 112D output values of the voltages applied to the load 132 and the shunt resistor 212, respectively, as values of the voltages that change according to the changes in the temperature of the load 132.

As described with regard to the first embodiment of the present disclosure, the voltage value applied to the load 132 or the shunt resistor 212 may be used to determine whether the aerosol source is insufficient in quantity. Since the second circuit 204 used to obtain the voltage value includes the shunt resistor 212, the second circuit 204 has an electric resistance value higher than that of the first circuit 202 used to generate the aerosol.

In the present embodiment, it is preferable that the shunt resistor 212 has an electric resistance value higher than that of the load 132. It is preferable that the aerosol generation device 100 measures a value of the voltage applied to the load 132 using the sensor 112B. The value of the voltage that changes according to the changes in temperature of the load 132 is obtained based on comparison between a value of the reference voltage and a value of an amplified voltage applied to the load 132. Hereinafter, the present embodiment will be described in connection with its specific examples.

It is assumed that a normal temperature is 25° C., the boiling point of the aerosol source is 200° C., and the temperature of the load 132 is 350° C. when it is determined that the aerosol source is insufficient in quantity (an overheated state). When the switch Q2 is in the on state and the second circuit 204 is functioning, a value of the current flowing through the shunt resistor 212 included in the second circuit 204 is equal to a value of the current flowing through the load 132 that is connected to the shunt resistor 212 in series. A current value $I_{Q2}$ at this time can be expressed as follows.

$$I_{Q2}=V_{out}/(R_{HTR}(T_{HTR})+R_{shunt})$$

Where "$V_{out}$" is a value of the voltage applied to the combined resistor formed of the shunt resistor 212 and the load 132 that are connected to each other in series. Note that when the aerosol generation device 100 does not include the conversion unit 208, "$V_{out}$" corresponds to the output voltage of the power supply 110. In addition, when the aerosol generation device 100 includes the conversion unit 208, "$V_{out}$" corresponds to the output voltage of the conversion unit 208. A difference $\Delta I_{Q2}$ between "$I_{Q2}$" at the normal temperature and "$I_{Q2}$" in the overheated state is expressed as follows.

$$\Delta I_{Q2}=V_{out}/(R_{HTR}(T_{R.T.})+R_{shunt})-V_{out}/(R_{HTR}(T_{delep.})+R_{shunt})$$

Where "$R_{HTR}(T_{R.T.})$" is a resistance value of the load 132 at the normal temperature, and "$R_{HTR}(T_{delep.})$" is a resistance value of the load 132 in the overheated state. As an example, when $V_{out}=2.0$ V, $R_{HTR}(T_{R.T.})=1\Omega$, $R_{HTR}(T_{delep.})=2\Omega$, and $R_{shunt}=199\Omega$, $\Delta I_{Q2}=0.05$ mA. In addition, the value $I_{Q2}(R_{.T.})$ of the current flowing through the second circuit 204 at the normal temperature is calculated to be 10.00 mA. The value $I_{Q2}(T_{delep.})$ of the current flowing through the second circuit 204 in the overheated state is calculated to be 9.95 mA.

In this example, the voltages $V_{shunt}(T_{R.T.})$ and $V_{shunt}(T_{delep.})$ applied to the shunt resistor 212 in the normal temperature state and the overheated state are 1990.00 mV and 1980.05 mV, respectively. A difference $|\Delta V_{shunt}|$ between the two is 9.95 mV. On the other hand, the voltages $V_{HTR}(T_{R.T.})$ and $V_{HTR}(T_{delep.})$ applied to the load 132 in the normal temperature state and the overheated state are 10.00 mV and 19.90 mV, respectively. A difference $|\Delta V_{HTR}|$ between the two is 9.90 mV.

Figure 7:
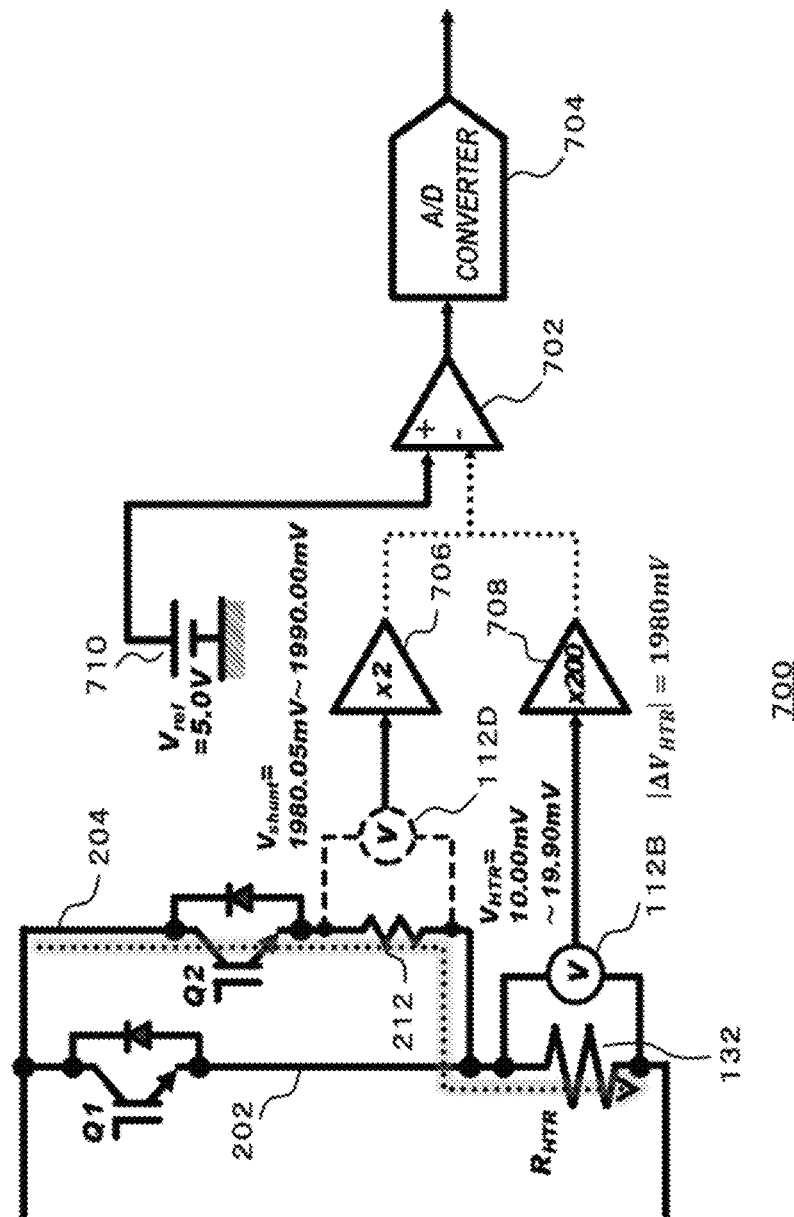
FIG. 7 is a diagram illustrating a circuit configuration for obtaining a value of a voltage that changes according to changes in temperature of a load, according to an embodiment of the present disclosure.

FIG. 7 illustrates a circuit configuration for obtaining a value of a voltage that changes according to changes in temperature of the load 132, according to an embodiment. A circuit 700 illustrated in FIG. 7 includes a comparator 702, an analog/digital converter 704, amplifiers 706 and 708, and a reference voltage power supply 710 in addition to the first circuit 202, the second circuit 204, the switches Q1 and Q2, the shunt resistor 212, the load 132, and the sensors 112B and 112D that form a part of the circuit 200 illustrated in FIG. 2. The circuit 700 does not necessarily include both of the sensors 112B and 112D, and it is only required that the circuit 700 includes any one of the sensors 112B and 112D. The circuit 700 also does not necessarily include both of the amplifiers 706 and 708, and it is only required that the circuit 700 includes any one of the amplifiers 706 and 708.

In the circuit 700, when the second circuit 204 is functioning (the current flows as indicated by the arrow), a difference (analog value) between the reference voltage $V_{ref}$ (analog value) output from the power supply 710 and the voltage (analog value) applied to the shunt resistor 212 or the load 132 is obtained by the comparator 702. A value of the voltage that changes according to changes in temperature of the load 132 is obtained by converting the difference into a digital value using the A/D converter 704. The reference voltage $V_{ref}$ can be set to approximately 5.0 V. When comparing with this reference voltage, it is preferable that the voltage value applied to the shunt resistor 212 or the load 132 is amplified to a value close to the reference voltage. In this example, since the voltage applied to the shunt resistor 212 is in the range of 1980.05 mV to 1990.00 mV, a possible amplification factor for comparing with the reference voltage is approximately two times. Accordingly, the difference of 9.95 mV between the applied voltage in the normal temperature state and the applied voltage in the overheated state is also amplified only to approximately two times. In contrast, since the voltage applied to the load 132 is in the range of 10.00 mV to 19.90 mV, a possible amplification factor for comparing with the reference voltage is approximately 200 times. Accordingly, the difference of 9.90 mV between the applied voltage in the normal temperature state and the applied voltage in the overheated state can be also amplified to approximately 200 times. Accordingly, the accuracy of distinguishing between the normal temperature state and the overheated state is higher when the applied voltage of the load 132 is measured than when the applied voltage of the shunt resistor 212 is measured. Accordingly, the applied voltage of the load 132 is measured, thereby improving the detection accuracy with respect to the insufficiency of the aerosol source.

In an example, the aerosol generation device 100 includes the conversion unit 208 that converts an output voltage of the power supply 110 and applies the converted output voltage to the second circuit 204 and the load 132. In this case, the acquisition unit may acquire a target value of the output voltage of the conversion unit 208 while the current flows through the second circuit 204. For example, the acquisition unit may acquire the target value stored in the memory 114. According to this configuration, it is not necessary to measure the voltage applied to the entire circuit by the sensor.

In an example, the conversion unit 208 is connected between a higher voltage node of nodes to which the first circuit 202 and the second circuit 204 are connected and the power supply 110. In this way, the conversion unit 208 is arranged upstream of the first circuit 202 for generating the aerosol and the second circuit 204 for measuring the voltage. Accordingly, the voltage applied to the load 132 can be highly controlled also in generation of the aerosol, whereby the inhaling flavor component and the like contained in the aerosol generated by the aerosol generation device 100 is stabilized.

As an example, the conversion unit 208 is a switching regulator (a buck converter) that can decrease and output the input voltage. Among regulators, the switching regulator is used, thereby improving the voltage conversion efficiency. Furthermore, this can prevent overvoltage from being applied to the circuit. Note that, to cause the first circuit 202 to function, the control unit 106 may control the conversion unit 208 so that the switching regulator which is the conversion unit 208 stops switching and outputs the input voltage as is without converting it. The control unit 106 controls the conversion unit 208 in a so-called direct connection mode, thereby causing no transition loss and no switching loss in the conversion unit 208 and improving the utilization efficiency of electric power stored in the power supply 110.

In an example, the storage unit 116A that stores the aerosol source, and the load 132 may be included in the cartridge 104A that can be attached/detached to/from the aerosol generation device 100, via the connecter. On the other hand, the sensor 112B is not included in the cartridge 104A, and may be included in the main body 102. That is, the sensor 112B may be configured to output a value of the voltage applied to the load 132 and the connecter, as a value of the voltage that changes according to the changes in temperature of the load 132. Thus, the cost of the disposable cartridge 104A can be reduced.

In an example, the aerosol base material 116B that retains the aerosol source may be included in the aerosol generating article 104B that is insertable/extractable into/from the aerosol generation device 100. On the other hand, the sensor 112B is not included in the aerosol generating article 104B, and may be included in the main body 102. Thus, the cost of the disposable aerosol generating article 104B can be reduced.

Hereinafter, the electric resistance value of the shunt resistor 212 in the present embodiment will be examined.

When the electric resistance value of the shunt resistor 212 is too large, the current hardly flows when the voltage values and the resistance values of the load 132 and the shunt resistor 212 are measured. As a result, the current value is buried in the error of the sensor. As a result, it makes it difficult to accurately measure the voltage value and the resistance value.

To avoid the above-described problem, in an example, the electric resistance value of the shunt resistor 212 (and the voltage applied to the entire circuit and the electric resistance value of the load 132) may be set so that a current having magnitude that allows distinguishing between the state in which the current flows through the second circuit 204 and the state in which no current flows through the second circuit 204 has such a value that the current flows through the second circuit 204. In this way, the electric resistance value of the shunt resistor 212 have such magnitude that the output values of the sensor 112B and the sensor 112D are not buried in the noise. Accordingly, this can prevent a detection error as to whether the aerosol source is insufficient in quantity.

As the power supply 110 is degraded, the output voltage of the power supply 110 also decreases. Accordingly, when the second circuit 204 is functioning, the value of the current flowing through the second circuit 204 decreases. Also, in the case where the voltage of the power supply 110 is a discharge termination voltage (the residual quantity 0%), it is desirable that the output values of the sensor 112B and the sensor 112D have such magnitude that the output values of the sensor 112B and the sensor 112D are not buried in the noise. For this purpose, in an example, the electric resistance value of the shunt resistor 212 (and the voltage applied to the entire circuit and the electric resistance value of the load 132) may be set so that a current having magnitude that allows distinguishing between the state in which the current flows through the second circuit 204 and the state in which no current flows through the second circuit 204 has such a value that the current flows through the second circuit 204 in the case where the voltage of the power supply 110 is a discharge termination voltage. This can prevent a detection error as to whether the aerosol source is insufficient in quantity.

As described above, the aerosol generation device 100 may include the conversion unit 208 that converts the output voltage of the power supply 110 and applies the converted voltage to the second circuit 204 and the load 132. In this case, the electric resistance value of the shunt resistor 212 (and the voltage applied to the entire circuit and the electric resistance value of the load 132) may be set so that a current having magnitude that allows distinguishing between the state in which the current flows through the second circuit 204 and the state in which no current flows through the second circuit 204 has such a value that the current flows through the second circuit 204 in the case where the output voltage of the conversion unit 208 is applied to the second circuit 204 and the load 132. This can prevent a detection error as to whether the aerosol source is insufficient in quantity.

In an example, the electric resistance value of the shunt resistor 212 (and the voltage applied to the entire circuit and the electric resistance value of the load 132) has such a value that a current having magnitude that allows distinguishing between the state in which the current flows through the second circuit 204 and the state in which no current flows through the second circuit 204 has such a value that the current flows through the second circuit 204 in the case where the temperature of the load 132 is an achievable temperature only when the aerosol source is insufficient in quantity. This can prevent a detection error even in the state that the current most hardly flows due to insufficiency of the aerosol source.

When the electric resistance value of the shunt resistor 212 is too small, the electric power higher than necessary is supplied to the load 132 when the voltage value of the load 132 is measured using the second circuit 204, which may cause generation of the aerosol. In this case, the aerosol source is consumed wastefully.

To solve the above-described problem, in an example, the electric resistance value of the shunt resistor 212 (and the voltage applied to the entire circuit and the electric resistance value of the load 132) may be set to have such a value that only the electric power required for heat retention of the load 132 is supplied to the load 132 while the current flows through the second circuit 204. In another example, the electric resistance value of the shunt resistor 212 (and the voltage applied to the entire circuit and the electric resistance value of the load 132) may be set to have such a value that the load 132 does not generate the aerosol while the current flows through the second circuit 204. These configurations can prevent the aerosol source from being consumed wastefully.

As an example, the electric resistance value of the shunt resistor 212 such that only the electric power required for heat retention of the load 132 is supplied to the load 132 while the current flows through the second circuit 204 will be examined with respect to the aerosol generation device 100A. Firstly, the amount of heat $Q$ required for heat retention of the load 132 per unit time is expressed as follows.

$$Q = (m_{wick} \times C_{wick}) \times (T_{B.P.} - \Delta T_{wick}) + \\ (m_{coil} \times C_{coil}) \times (T_{B.P.} - \Delta T_{coil}) + (m_{liquid} \times C_{liquid}) \times (T_{B.P.} - \Delta T_{liquid})$$

"$m_{wick}$," "$m_{coil}$," and "$m_{liquid}$" are masses of the aerosol sources retained in the retention unit 130, the load 132, and the retention unit 130, respectively. "$C_{wick}$," "$C_{coil}$," and "$C_{liquid}$" are specific heats of the aerosol sources retained in the retention unit 130, the load 132, and the retention unit 130, respectively. "$-\Delta T_{wick}$," "$-\Delta T_{coil}$," and "$-\Delta T_{liquid}$" are temperature decreases per unit time of the retention unit 130, the load 132, and the retention unit 130, respectively. In addition, "$T_{B.P.}$" is a boiling point of the aerosol source.

Note that for the sake of simplicity, "$\Delta T_{wick}$," "$\Delta T_{coil}$," and "$\Delta T_{liquid}$" may be regarded as all the same value $\Delta T$. "Q" in this case is expressed as follows.

$$Q=(m_{wick} \times C_{wick}+m_{coil} \times C_{coil}+m_{liquid} \times C_{liquid}) \times (T_{B.P.}-\Delta T)$$

The expression in parenthesis is replaced with "$\Sigma m \times C$", "Q" is expressed as follows.

$$Q=(\Sigma m \times C) \times (T_{B.P.}-\Delta T)$$

The electric power W consumed in the load 132 while the current flows through the second circuit 204 is expressed by the following expression.

$$W = V_{HTR} \times I_{Q2}$$
$$= (V_{out} - V_{shunt}) \times I_{Q2}$$
$$= (V_{out} - I_{Q2} \times R_{shunt}) \times I_{Q2}$$

Where "$V_{HTR}$" is a value of the voltage applied to the load 132, "$I_{Q2}$" is a value of the current flowing through the second circuit, "$V_{out}$" is a value of the voltage applied to a combined resistor formed of the shunt resistor 212 and the load 132 that are connected to each other in series, "$V_{shunt}$" is a value of the voltage applied to the shunt resistor 212, and "$R_{shunt}$" is an electric resistance value of the shunt resistor 212.

That is, in order to ensure that only the electric power required for heat retention of the load 132 is supplied to the load 132 while the current flows through the second circuit 204, it is necessary to satisfy the following equation.

$$W=Q$$

When the above-described expression is substituted into "W" to thereby obtain the electric resistance value $R_{shunt}$ of the shunt resistor 212, the electric resistance value $R_{shunt}$ is expressed as follows.

$$(V_{out} - I_{Q2} \times R_{shunt}) \times I_{Q2} = Q$$
$$-R_{shunt} \times I_{Q2}^2 + V_{out} \times I_{Q2} = Q$$
$$R_{shunt} = V_{out} / I_{Q2} - Q / I_{Q2}^2$$
$$= (V_{out}/V_{HTR}) \times R_{HTR} - (R_{HTR}/V_{HTR})^2 \times Q$$

Accordingly, it is only required that the electric resistance value of the shunt resistor 212 (and the voltage applied to the entire circuit and the electric resistance value of the load 132) is set to satisfy the above expression. Note that "$V_{BTR}$" may be regarded as a value obtained by multiplying "$V_{out}$" by a predetermined coefficient smaller than 1. Furthermore, since an ideal model is used for this examination and an approximation is performed, "$\pm \Delta$" serving as a correction term may be introduced into the above expression.

The switch Q1 is used to connect and disconnect the electrical conduction of the first circuit 202. The switch Q2 is used to connect and disconnect the electrical conduction of the second circuit 204. In an example, the control unit 106 may control switching of the switches Q1 and Q2 so that an on time of the switch Q1 is longer than that of the switch Q2. A time period (on time) from when the switch Q2 is switched to the on state until the switch Q2 is switched to the off state can be the minimum time period that can be achieved by the control unit 106. According to such a configuration, the time period during which the switch Q2 is in the on state to measure the voltage of the load 132 or the shunt resistor 212 is shorter than the time period during which the switch Q1 is in the on state to generate the aerosol. Accordingly, the aerosol source can be prevented from being consumed wastefully.

As an example, the aerosol generation device according to the present embodiment may be manufactured according to the method including the following steps.

Step of arranging the load 132 generates heat upon receipt of electric power from the power supply 110 and atomizes an aerosol source using the heat, and in which an electric resistance value changes in response to a temperature Step of forming the first circuit 202 used to cause the load 132 to atomize the aerosol source Step of forming the second circuit 204 used to detect a voltage that changes according to changes in temperature of the load 132, connected to the first circuit 202 in parallel, and having an electric resistance value higher than that of the first circuit 202

Step of arranging an acquisition unit that acquires a value of a voltage applied to the second circuit 204 and the load 132

Step of arranging the sensor 112B (or the sensor 112D) that outputs the value of a voltage that changes according to the changes in temperature of the load 132

Third Embodiment

When the aerosol source stored in the storage unit 116A is insufficient in quantity, it is necessary to replace the cartridge 104A. Similarly, when the aerosol source carried in the aerosol base material 116B is insufficient in quantity, it is necessary to replace the aerosol generating article 104B. The resistance value of the heater (the load 132) included in the cartridge 104A (or the aerosol generating article 104B) has a manufacturing variation. Accordingly, if the same settings (for example, a threshold related to the resistance value of the load 132, the threshold related to the voltage value of the load 132, and the like) are used for all of the cartridges 104A to detect insufficiency of the aerosol source, the insufficiency of the aerosol source cannot be detected with high accuracy in some cases. In this case, a problem from the viewpoint of safety may arise in that the aerosol generation device 100 causes unintended behavior or the like. The present inventors have recognized such a problem as a new problem. An object of a third embodiment of the present disclosure is to solve such a new problem and to provide an aerosol generation device with further improved detection accuracy as to whether the aerosol source is insufficient in quantity.

Figure 8:
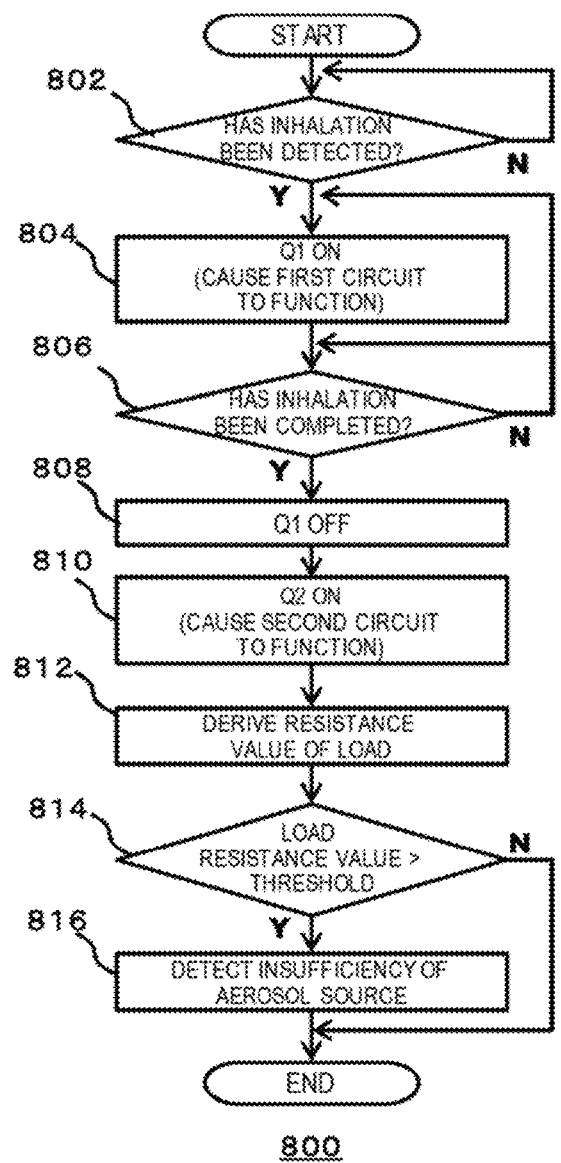
FIG. 8 is a flowchart of exemplary processing of detecting insufficiency of the aerosol source.

FIG. 8 is a flowchart of exemplary processing of detecting insufficiency of the aerosol source. Here, all the steps will be described as being performed by the control unit 106. However, it should be noted that some of the steps may be performed by another component in the aerosol generation device 100. Note that the present embodiment is described using the circuit 200 illustrated in FIG. 2 as an example, but it is apparent to those skilled in the art that the description can be made using another circuit. This is applicable to the following other flowcharts.

The process starts at step 802. In step 802, the control unit 106 determines whether the user's inhalation has been detected, based on the information obtained from the pressure sensor, the flow sensor, and the like. For example, when the output values of these sensors continuously change, the control unit 106 may determine that the user's inhalation has been detected. Alternatively, the control unit 106 may determine that the user's inhalation has been detected, based on a fact that a button for starting the generation of the aerosol has been pressed, etc.

When it is determined that the inhalation has been detected ("Y" in step 802), the process proceeds to step 804. In step 804, the control unit 106 switches the switch Q1 to the on state to cause the first circuit 202 to function.

The process proceeds to step 806, and the control unit 106 determines whether the inhalation has been completed. When it is determined that the inhalation has been completed ("Y" in step 806), the process proceeds to step 808.

In step 808, the control unit 106 switches the switch Q1 to the off state. In step 810, the control unit 106 switches the switch Q2 to the on state to cause the second circuit 204 to function.

The process proceeds to step 812, and the control unit 106 derives a resistance value of the load 132. For example, the control unit 106 may detect a value of the current flowing through the second circuit 204 and derive the resistance value of the load 132 based on the detected value of the current.

The process proceeds to step 814, and the control unit 106 determines whether the resistance value of the load 132 exceeds a predetermined threshold. The threshold may be set to a resistance value when the temperature of the load 132 reaches a predetermined temperature higher than a boiling point of the aerosol source. When it is determined that the resistance value of the load exceeds the threshold ("Y" in step 814), the process proceeds to step 816, and the control unit 106 determines that the aerosol source in the aerosol generation device 100 is insufficient in quantity. On the other hand, when it is determined that the resistance value of the load does not exceed the threshold ("N" in step 814), it is not determined that the aerosol source is insufficient in quantity.

It should be noted that FIG. 8 illustrates an example of a general flow for determining whether the aerosol source in the aerosol generation device 100 is insufficient in quantity.

Figure 9:
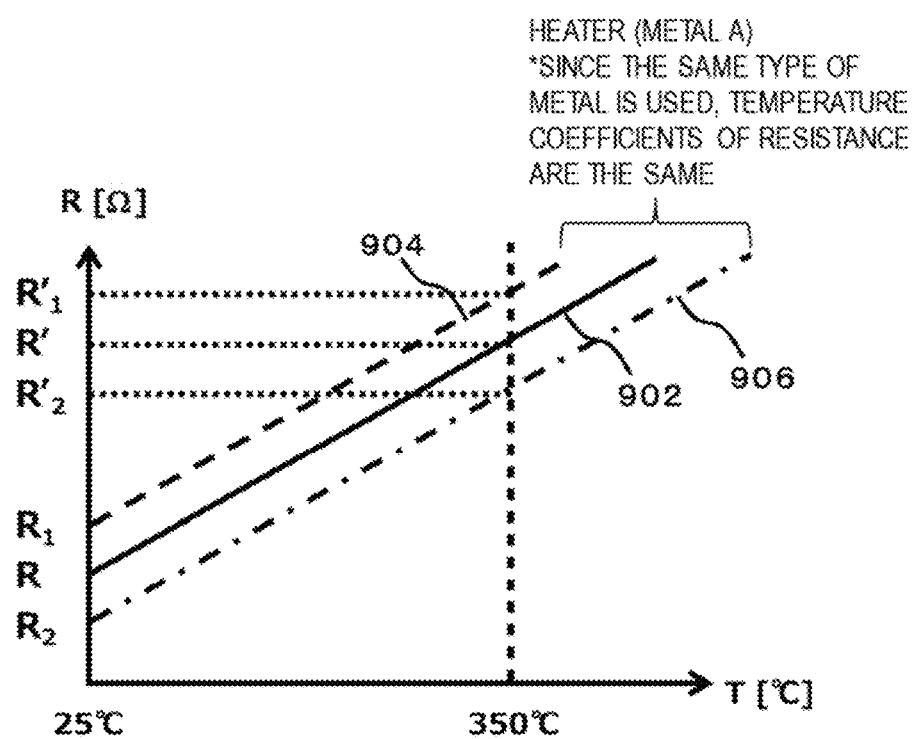
FIG. 9 is a graph showing an example of a relationship between an electric resistance value and a temperature of each of the loads made of the same metal.

FIG. 9 is a graph showing an example of a relationship between an electric resistance value and a temperature of each of the loads (heaters) 132 made of the same metal A. Basically, the temperature and the electric resistance value of the load 132 are in a proportional relationship. Since the resistance value of the load 132 has a manufacturing variation, as shown in the figure, the loads 132 may obtain resistance values such as R, $R_1$, and $R_2$ that are different from one individual to another, at the room temperature (for example, 25° C.). When 350° C. is used as the temperature threshold of the load 132 which is the criterion for determining whether the aerosol source is insufficient in quantity, as shown in the figure, thresholds of the resistance values of the loads 132 which are the criterion for determining whether the aerosol source is insufficient in quantity are values R', $R_1'$, and $R_2'$ which are different from one individual to another.

The configuration of the aerosol generation device according to the present embodiment is basically the same as the configurations of the aerosol generation device 100 illustrated in FIG. 1A and FIG. 1B and the circuit 200 illustrated in FIG. 2. In an example, the aerosol generation device includes the power supply 110, the load 132 that generates heat upon receipt of electric power from the power supply 110 and atomizes an aerosol source using the heat, and has a temperature-resistance value characteristic as shown in FIG. 9 in which an electric resistance value changes in response to a temperature, a memory 114 that stores the temperature-resistance value characteristic, a sensor that outputs a value (an electric resistance value, a current value, a voltage value, or the like) related to the resistance value of the load 132, and a control unit configured to calibrate the stored temperature-resistance value characteristic based on correspondence between an output value of the sensor and an estimate of the temperature of the load 132 corresponding to the output value.

According to the present embodiment, the PTC characteristic of the cartridge 104A (or the aerosol generating article 104B) is calibrated based on the association between the electric resistance value and the temperature of the load 132. Accordingly, even when an individual difference exists in the PTC characteristic of the cartridge 104A (or the aerosol generating article 104B), the PTC characteristic can be calibrated to a correct value. It should be noted that even when the load 132 has the NTC characteristic, the NTC characteristic can be calibrated in the same manner.

Figure 10:
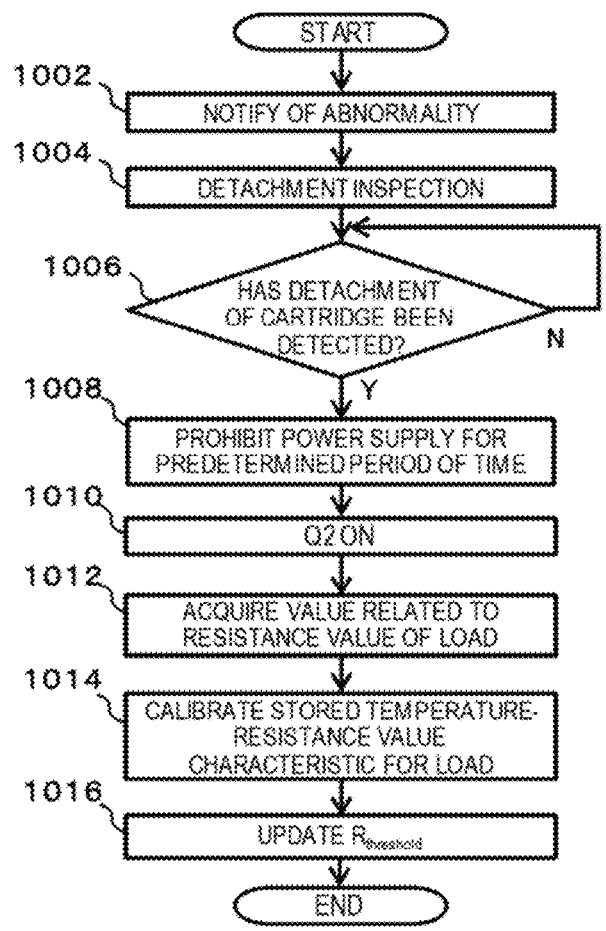
FIG. 10 is a flowchart of exemplary processing of calibrating a temperature-resistance value characteristic of the load, according to an embodiment of the present disclosure.

FIG. 10 is a flowchart of exemplary processing of calibrating a temperature-resistance value characteristic of the load 132, according to an embodiment of the present disclosure. Here, it is assumed that the aerosol generation device of the present embodiment has the same configuration of the aerosol generation device 100A illustrated in FIG. 1A or the aerosol generation device 100B illustrated in FIG. 1B. However, it is apparent to those skilled in the art that the same processing can be applied to various aerosol generation devices having the other configurations.

Figure 5:
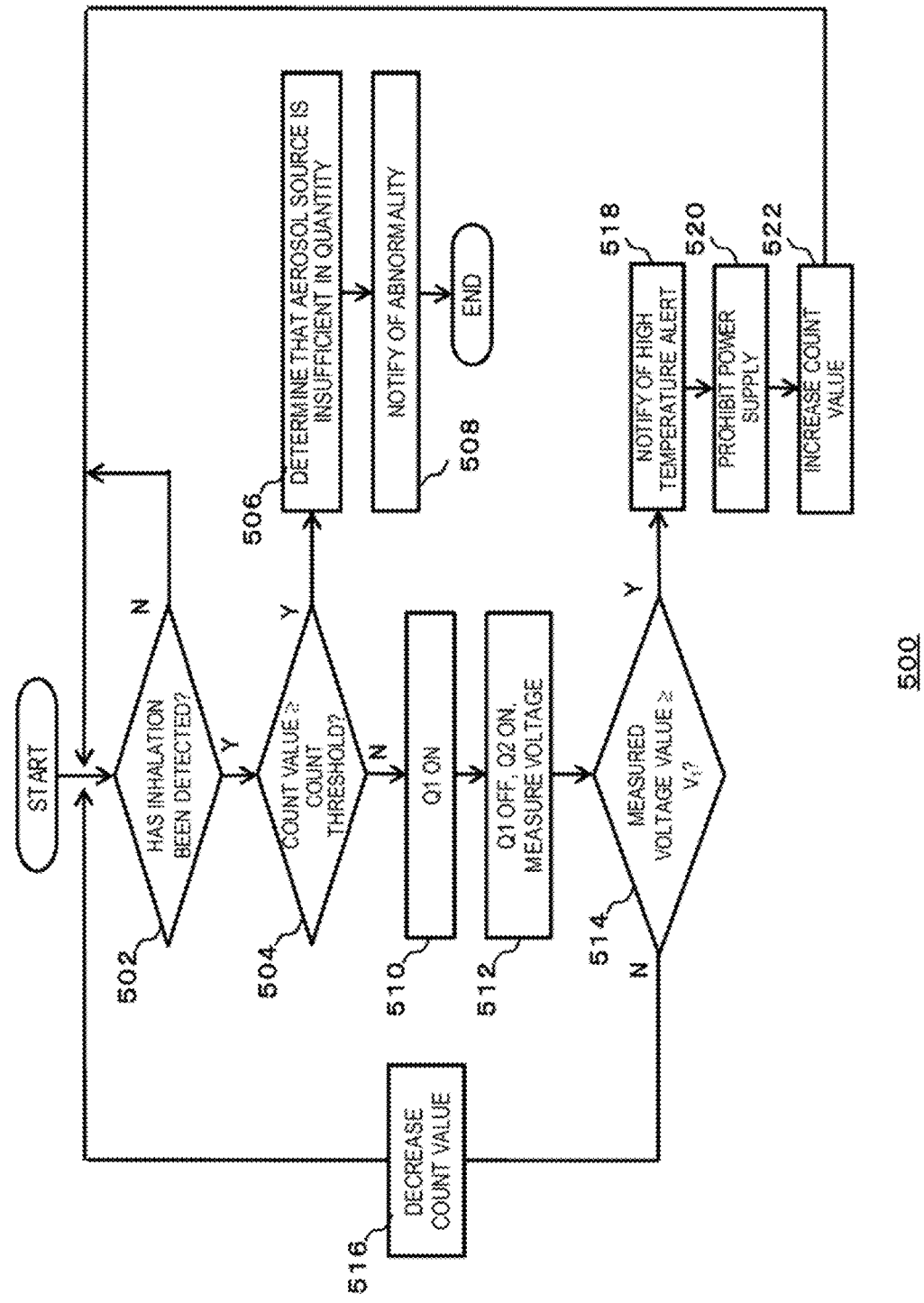
FIG. 5 is a flowchart of exemplary processing of determining whether the aerosol source is insufficient in quantity, according to an embodiment of the present disclosure.
Figure 6:
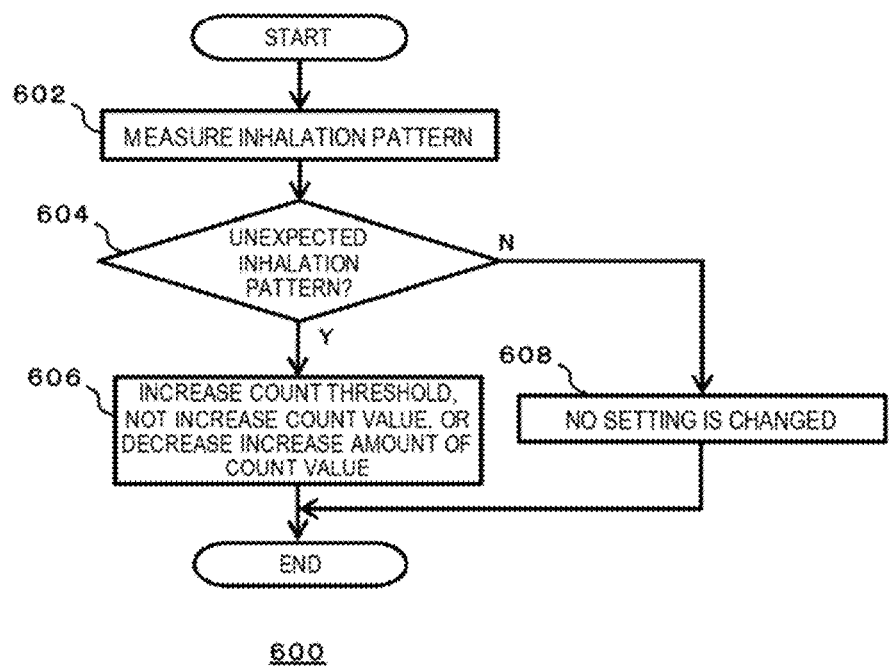
FIG. 6 is a flowchart of exemplary processing performed when a user's inhalation pattern is an unexpected pattern, according to an embodiment of the present disclosure.

The process in step 1002 is the same as the processes in step 308 of FIG. 3, step 408 of FIG. 4, and step 508 of FIG. 5 in relation to the first embodiment. The control unit 106 performs a control to notify the user of the abnormality. For example, the control unit 106 causes the notifying unit 108 to perform the operation such as light emission, display, sound production, or vibration. In this case, in order to generate the aerosol using the aerosol generation device 100, the user needs to detach the cartridge 104A (or the aerosol generating article 104B) and replace with a new cartridge.

The process proceeds to step 1004, and the control unit 106 performs a detachment inspection for detecting whether the cartridge 104A has been detached. In an example, the aerosol generation device 100 may include a connecter that allows the attachment/detachment of the cartridge 104A or the insertion/extraction of the aerosol generating article 104B. The control unit 106 may calibrate the stored temperature-resistance value characteristic only when detecting the detachment of the cartridge 104A from the connecter or the extraction of the aerosol generating article 104B from the connecter. This can prevent calibration from being performed at a wrong timing.

Thus, the control unit 106 may determine whether to perform the calibration based on a predetermined condition, prior to the calibration of the stored temperature-resistance value characteristic. In an example, the control unit 106 may store the resistance value of the cartridge 104A detached from the connecter or the resistance value of the aerosol generating article 104B extracted from the connecter. The above-described predetermined condition may be that the resistance value stored in the control unit 106 is different from the resistance value of the cartridge 104A newly attached to the connecter or the resistance value of the aerosol generating article 104B newly inserted into the connecter. In another example, the above-described predetermined condition may be that a rate of change in the resistance value of the cartridge 104A attached to the connecter or a rate of change in the resistance value of the aerosol generating article 104B inserted into the connecter is lower than a predetermined threshold while the power supply to the load 132 is continued. With these configurations, an unnecessary calibration can be suppressed in the case where the cartridge 104A or the aerosol generating article 104B that has been once detached is connected again or the like. In addition, in an example, the above-described predetermined condition may be that from correspondence between an output value of the sensor and an estimate of the temperature of the load 132 corresponding to the output value, it is determined that the temperature of the load 132 is estimated smaller than an actual value if the stored temperature-resistance value characteristic is not calibrated.

In step 1006, the control unit 106 determines whether the detachment of the cartridge 104A (or the extraction of the aerosol generating article 104B) has been detected, based on the result of the process in step 1004. Note that in step 1006, the control unit 106 may determine whether the attachment of the cartridge 104A (or the insertion of the aerosol generating article 104B) has been detected, after the detachment of the cartridge 104A (or the extraction of the aerosol generating article 104B). In addition, only when the attachment of the cartridge 104A (or the insertion of the aerosol generating article 104B) has been detected, the process may proceed to step 1008.

When the detachment of the cartridge 104A has been detected ("Y" in step 1006), the process proceeds to step 1008. In step 1008, the control unit 106 prohibits the power supply to the load 132 for a predetermined period of time. The predetermined period of time can be, for example, a period of time sufficient for the temperature of the load 132 to be the room temperature.

The process proceeds to step 1010, and the control unit 106 switches the switch Q2 to the on state. This causes the second circuit 204 to function.

The process proceeds to step 1012, and the control unit 106 acquires a value related to the resistance value of the load 132. For example, the aerosol generation device 100A may include a current sensor for detecting a value of the current flowing through the second circuit 204. The control unit 106 may acquire a resistance value of the load 132 based on the value of the current and a voltage value obtained by the sensor 112B. Alternatively, as described in relation to the first embodiment, in step 1012, the control unit 106 may acquire a voltage value of the load 132 using the sensor 112B.

The process proceeds to step 1014, and the control unit 106 calibrates the stored temperature-resistance value characteristic for the load 132. For example, it is assumed that the temperature-resistance value characteristic 902 shown in FIG. 9 has been stored in the memory before the processing 1000 is performed. When a resistance value of the load 132 at the room temperature is $R_1$, the resistance value being acquired in step 1008, the control unit 106 may use the temperature-resistance value characteristic 904 instead of the temperature-resistance value characteristic 902 in step 1014.

In step 1014, the control unit 106 may calibrate an intercept of the stored temperature-resistance value characteristic (R, $R_1$, and $R_2$ in the case of an example shown in FIG. 9). Since only the intercept of the PTC characteristic is calibrated, it is only required that the information of only one point of the relationship between the resistance value and the temperature is acquired, thereby allowing faster calibration.

In an example, the aerosol generation device 100 may include database that stores an electric resistance value of the load 132 and one of an inclination and an intercept of the temperature-resistance value characteristic corresponding to the electric resistance value, for each type of the load 132. The control unit 106 may calibrate one of the inclination and the intercept of the temperature-resistance value characteristic based on the output value of the sensor and the database. In addition, the control unit 106 may calibrate the other of the inclination and the intercept of the temperature-resistance value characteristic based on the output value of the sensor and one of the inclination and the intercept of the calibrated temperature-resistance value characteristic. In another example, the above-described database may be positioned outside the aerosol generation device 100, and the control unit 106 may obtain necessary information by communicating with the database or the like.

In an example, the above-described database may store an electric resistance value of the load 132 at the room temperature or the temperature at which the aerosol is generated and the other of the inclination and the intercept of the temperature-resistance value characteristic corresponding to the electric resistance value, for each type of the load 132.

The process proceeds to step 1016, and the control unit 106 updates a threshold $R_{threshold}$ of the resistance value used for determining whether the aerosol source is insufficient in quantity (for example, step 814 of FIG. 8). In the above-described example, the value of $R_{threshold}$ is changed from "R'" to "$R_1$'".

Thus, in an example, the control unit 106 may calibrate the stored temperature-resistance value characteristic based on correspondence between an output value (a voltage value, a current value, a resistance value, or the like) of the sensor before the load 132 generates the aerosol and the room temperature. Since the PTC characteristic is calibrated based on the room temperature, the calibration accuracy with respect to the PTC characteristic is improved.

In addition, in an example, when the predetermined condition by which it is determined that the temperature of the load 132 is the room temperature is established, the control unit 106 may calibrate the stored temperature-resistance value characteristic based on the correspondence between an output value of the sensor before the load 132 generates the aerosol and the room temperature. In this way, the calibration is performed when the condition by which it is probable that the temperature of the load 132 has reached the room temperature is established. Accordingly, the possibility that the temperature of the load at the time of calibration is certainly the room temperature increases, whereby the calibration accuracy with respect to the PTC characteristic is improved.

In an example, the predetermined condition may be that a predetermined period of time has elapsed since the previous aerosol generation. As a result, a fact that the predetermined period of time has elapsed since the previous aerosol generation becomes the condition for regarding the temperature of the load as the room temperature. Accordingly, the load at the time of calibration is sufficiently cooled, whereby the possibility that the temperature of the load is settled to the room temperature increases.

In an example, the aerosol generation device 100 may include the cartridge 104A that includes the load 132 and the storage unit 116A for storing the aerosol source or the aerosol generating article 104B that includes the load 132 and the aerosol base material 116B for retaining the aerosol source, and the connecter that allows the attachment/detachment of the cartridge 104A or the insertion/extraction of the aerosol generating article 104B. The above-described predetermined condition may be that a predetermined period of time has elapsed since the attachment of the cartridge 104 to the connecter or the insertion of the aerosol generating article 104B into the connecter. In this way, a fact that the predetermined period of time has elapsed since the connection of the cartridge 104A becomes the condition for regarding the temperature of the load as the room temperature. Accordingly, the temperature of the load at the time of calibration is sufficiently cooled, whereby the possibility that the temperature of the load is settled to the room temperature increases.

In an example, the aerosol generation device 100 may include, as the sensor 112, the temperature sensor that outputs a temperature of an electric component forming the main body 102 including the power supply 110, the control unit 106, and the like or any one of a temperature inside the main body 102 and an ambient temperature of the main body 102. The above-described predetermined condition may be that the temperature output by the sensor 112 is the room temperature or an absolute value of a difference between the temperature output by the sensor 112 and the room temperature is equal to or less than the predetermined threshold. Such a condition may be also the condition for regarding the temperature of the load as the room temperature. Accordingly, when the temperature output by the sensor 112 is the temperature of the power supply 110 and the temperature of the control unit 106 or the temperature inside the main body 102, the aerosol generation device 100 is not functioning or is in a standby mode with low power consumption. In other words, the aerosol generation device 100 is in a state in which the electric power is not supplied to the load 132, whereby the temperature of the load at the time of calibration is sufficiently cooled, and the possibility that the temperature of the load is settled to the room temperature increases. In addition, when the temperature output by the sensor 112 is the ambient temperature of the main body 102, the aerosol generation device 100 is not left under an environment in which an absolute value of a difference between the temperature output by the sensor 112 and the room temperature rather than the room temperature including high temperature and low temperature is large, whereby the possibility that the temperature of the load at the time of calibration is settled to the room temperature increases.

In an example, when the above-described predetermined condition is satisfied, the control unit 106 may control the load 132 not to generate the aerosol until an output value of the sensor is associated with an estimate of the temperature corresponding to the output value. It will be appreciated that the temperature-resistance value characteristic may or may not be calibrated in response to the output value of the sensor. According to this configuration, the aerosol is not generated until the resistance value is measured. Accordingly, it is possible to prevent the occurrence of a situation that the temperature of the load at the time of calibration is greatly higher than the room temperature. Furthermore, since the aerosol is not generated using the temperature-resistance value characteristic before the calibration, detracting from the inhaling flavor of the aerosol can be prevented.

In an example, the control unit 106 may supply predetermined electric power from the power supply 110 to the load 132, the predetermined electric power being smaller than electric power required to increase the temperature of the load 132 to a temperature at which the load 132 can generate the aerosol. Furthermore, the control unit may calibrate the temperature-resistance value characteristic based on the output value output by the sensor while the predetermined electric power is supplied to the load 132.

In an example, the above-described predetermined electric power may be electric power that does not cause the temperature of the load 132 to increase over the resolution of the sensor. In another example, the above-described predetermined electric power may be electric power that does not cause the temperature of the load 132 to increase.

In an example, the control unit 106 may calibrate the inclination and the intercept of the stored temperature-resistance value characteristic based on the correspondence between an output value of the sensor and an estimate of the temperature of the load 132 corresponding to the output value and information (for example, a coefficient indicating the inclination of the temperature-resistance value characteristic) about the load 132 or the cartridge 104A including the load 132. In this way, not only the intercept but also the inclination is calibrated also based on the information about the cartridge 104A. Accordingly, even when a different cartridge including the load 132 made of different metal is connected, the calibration can be performed with high accuracy for each cartridge.

In an example, the control unit 106 may acquire the information about the load 132 or the cartridge 104A from at least one of communication with the external terminal, identification information of the load 132, identification information of the cartridge 104A or a package of the cartridge 104A, and a user input.

Figure 11A:
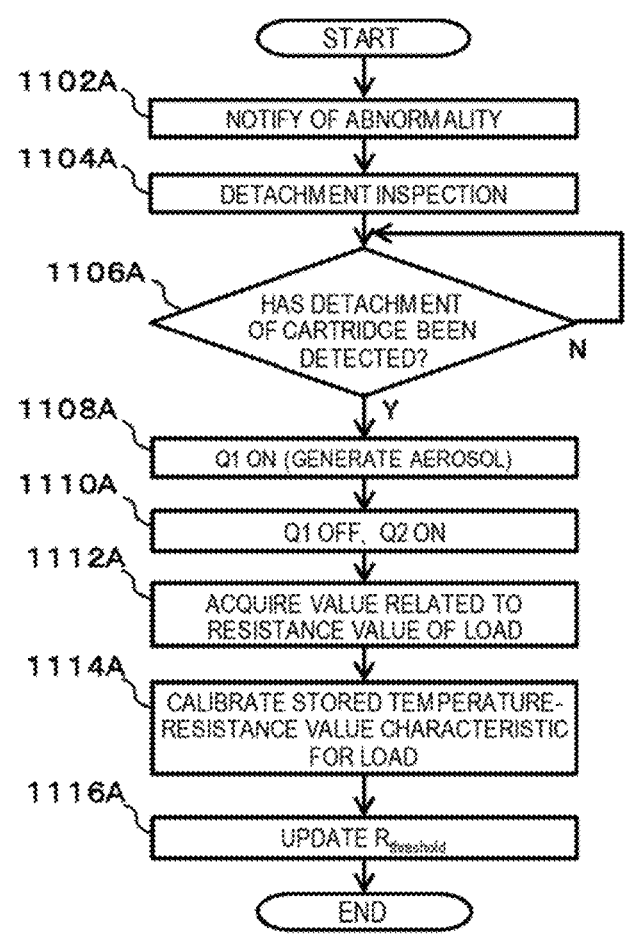
FIG. 11A is a flowchart of exemplary processing of calibrating a temperature-resistance value characteristic of the load, according to an embodiment of the present disclosure.

FIG. 11A is a flowchart of exemplary processing of calibrating a temperature-resistance value characteristic of the load, according to an embodiment of the present disclosure.

The processes in steps 1102A to 1106A are the same as the processes in steps 1002 to 1006 in an example of FIG. 10, and description thereof is omitted.

When the detachment of the cartridge 104A has been detected ("Y" in step 1106A), the process proceeds to step 1108A. In step 1108A, when detecting the user's inhalation, the control unit 106 switches the switch Q1 to the on state. Accordingly, this causes the first circuit 202 to function, whereby the aerosol is generated.

The process proceeds to step 1110A, and the control unit 106 switches the switch Q1 to the off state, and the switch Q2 to the on state. Accordingly, this causes the first circuit 202 not to function, but instead causes the second circuit 204 to function. The processes in steps 1112A to 1116A are the same as the processes in steps 1012 to 1016 of FIG. 10, and description thereof is omitted.

Figure 11B:
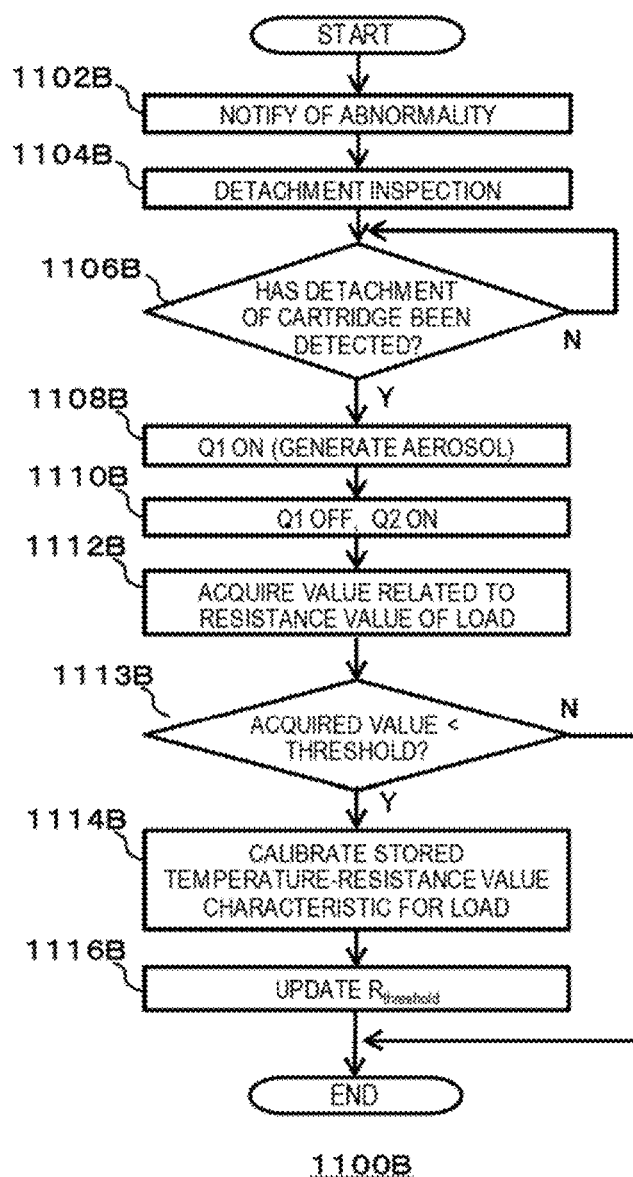
FIG. 11B is a flowchart of exemplary processing of calibrating a temperature-resistance value characteristic of the load, according to an embodiment of the present disclosure.

FIG. 11B is a flowchart of exemplary processing of calibrating a temperature-resistance value characteristic of the load, according to an embodiment of the present disclosure.

The processes in steps 1102B to 1112B are the same as the processes in steps 1012A to 1112A of FIG. 11A, and description thereof is omitted.

In step 1113B, the control unit 106 determines whether a value acquired in step 1112B is lower than the predetermined threshold. For example, the resistance value of the load 132 when the temperature of the load 132 reaches a temperature (for example, 300° C.) higher than the boiling point of the aerosol source may be set as the threshold. By performing the determination in step 1113B, the control unit 106 can determine whether the load 132 is in a state of generating the aerosol or a state of not generating the aerosol due to the insufficiency of the aerosol source.

When an acquired value is lower than the threshold ("Y" in step 1113B), the process proceeds to step 1114B. The processes in steps 1114B and 1116B are the same as the processes in steps 1114A and 1116A, and description thereof is omitted.

When the acquired value is equal to or higher than the threshold ("N" in step 1113B), the processes of steps 1114B and 1116B are not performed, and then the processing 1110B ends.

Thus, according to the present embodiment, in an example, the control unit 106 calibrates the stored temperature-resistance value characteristic based on the correspondence between the output value of the sensor when the electric power sufficient for aerosol generation is supplied to the load 132 and the temperature causing the aerosol generation. Since the PTC characteristic is calibrated based on the aerosol generation temperature, the calibration accuracy with respect to the PTC characteristic is improved.

In an example, when the output value of the sensor when the electric power sufficient for aerosol generation is supplied to the load 132 is equal to or higher than the threshold, the control unit 106 does not calibrate the stored temperature-resistance value characteristic. In this manner, when the temperature (resistance value) of the load is extremely high, the PTC characteristic is not calibrated. Accordingly, since the control unit 106 does not erroneously recognize that the excessively high temperature of the load when the aerosol source is depleted is the aerosol generation temperature, the calibration accuracy with respect to the PTC characteristic can be prevented from being drastically deteriorated. Alternatively, in another example, when a change amount in the output value of the sensor when the predetermined electric power is supplied to the load 132 is equal to or higher than the threshold, the control unit 106 does not calibrate the stored temperature-resistance value characteristic. In this way, when the temperature (resistance value) of the load extremely changes, the PTC characteristic is not calibrated. Accordingly, when the aerosol source is depleted, which may cause an extreme change in temperature of the load, the PTC characteristic is not calibrated, whereby the calibration accuracy with respect to the PTC characteristic can be prevented from being drastically deteriorated.

In an example, the control unit 106 calibrates the stored temperature-resistance value characteristic based on the correspondence between the output value of the sensor when the electric power sufficient for aerosol generation is supplied to the load 132 and is in the steady state at a value other than the room temperature, and the temperature causing the aerosol generation.

Figure 12:
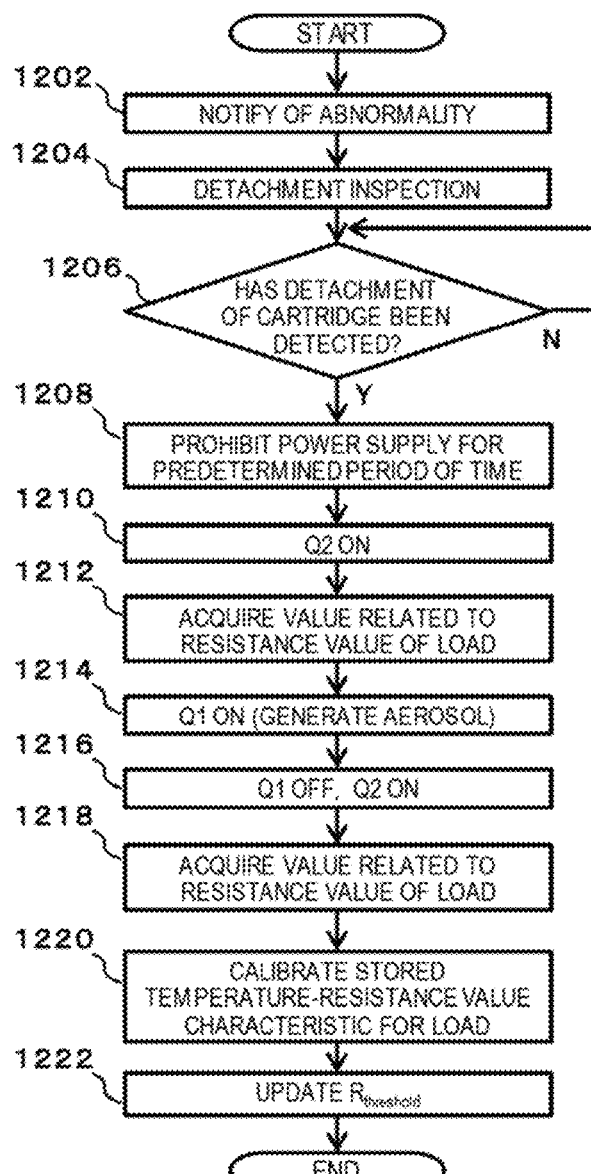
FIG. 12 is a flowchart of exemplary processing of calibrating a temperature-resistance value characteristic of the load, according to an embodiment of the present disclosure.

FIG. 12 is a flowchart of exemplary processing of calibrating a temperature-resistance value characteristic of the load, according to an embodiment of the present disclosure.

The processes in steps 1202 to 1212 are the same as the processes in steps 1002 and 1012 of FIG. 10. The processes in steps 1214 to 1218 are the same as the processes in steps 1108A and 1112A of FIG. 11A. In the flow of FIG. 12, these both processes are performed, and then the process proceeds to step 1220. In step 1220, the control unit 106 calibrates the inclination and the intercept of the stored temperature-resistance value characteristic based on the correspondence (obtained in steps 1208 to 1212) between an output value of the sensor before the load 132 generates the aerosol and the room temperature and the correspondence (based in step 1214 to step 1218) between an output value of the sensor when the electric power sufficient for aerosol generation is supplied to the load 132 and the temperature causing the aerosol generation. That is, the intercept and the inclination of the PTC characteristic are calibrated using two plots of (the temperature and the resistance value). Accordingly, the intercept and the inclination of the PTC characteristic can be calibrated with a simpler method without the necessity of having a dedicated information acquisition unit (for example, without the necessity of embedding the information necessary for calibration in the cartridge 104A).

Similarly to the example of FIG. 11B, in the above-described example, when the output value of the sensor when the electric power sufficient for aerosol generation is supplied to the load 132 is equal to or higher than the threshold, the control unit 106 need not calibrate the stored temperature-resistance value characteristic.

Figure 13:
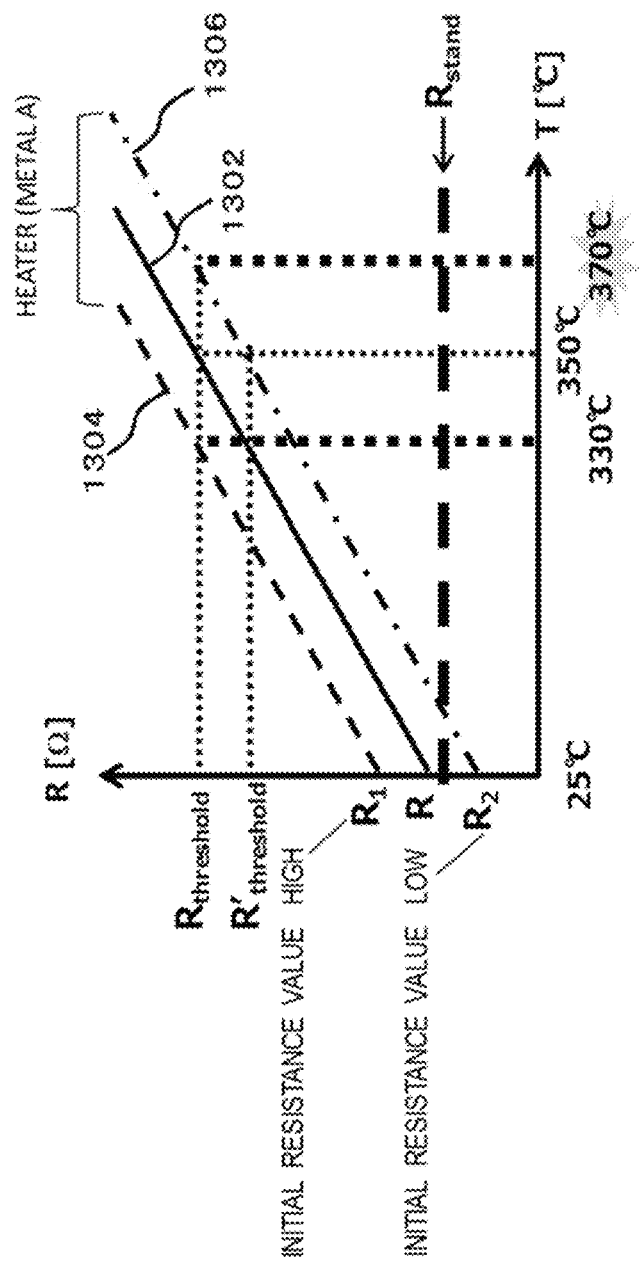
FIG. 13 is a graph showing that a temperature threshold for determining that the aerosol source is insufficient in quantity may become too high due to a manufacturing variation of the load 132.

FIG. 13 is a graph showing that a temperature threshold for determining that the aerosol source is insufficient in quantity may become too high due to a manufacturing variation of the load 132. The three straight lines shown in FIG. 13 indicate the temperature-resistance value characteristics of the loads (heaters) 132 made of the same type of metal A. Here, a solid line 1302 indicates a characteristic of a standard first load 132-1 having an initial resistance value R, a dotted line 1304 indicates a characteristic of a second load 132-2 having an initial resistance value $R_1$ that is higher than that of the standard one, and a dash dotted line 1306 indicates a characteristic of a second load 132-3 having an initial resistance value $R_2$ that is lower than that of the standard one. In addition, it is assumed that it is determined that the aerosol source is insufficient in quantity when the boiling point of the aerosol source is 200° C., and the temperature of the first load 132-1 is 350° C. In this case, as can be appreciated from the figure, a threshold of the resistance value of the load for determining whether the aerosol source is insufficient in quantity is $R_{threshold}$. In the case of the second load 132-2, the resistance value is $R_{threshold}$ when the temperature of the load reaches 330° C. Accordingly, since the alert is provided to the user at the temperature lower than the standard temperature threshold 350° C. even when "$R_{threshold}$" is used as a threshold, the overheating state does not occur. Accordingly, regarding the second load 132-2, it can be said that the calibration of the temperature-resistance value characteristic is not necessarily required. On the other hand, in the case of the third load 132-3, the resistance value becomes "$R_{threshold}$" after the temperature of the load reaches 370° C. Accordingly, when "$R_{threshold}$" is used as a threshold, the alert is not provided until the temperature of the load 132-3 reaches 370° C. which is very high temperature, resulting that the overheating state may occur. Accordingly, regarding the second load 132-3, it is necessary to calibrate the temperature-resistance value characteristic. In an example, only when the initial resistance value of the load 132 is below "$R_{stand}$" shown in FIG. 13, the temperature-resistance value characteristic of the load 132 may be calibrated.

Figure 14:
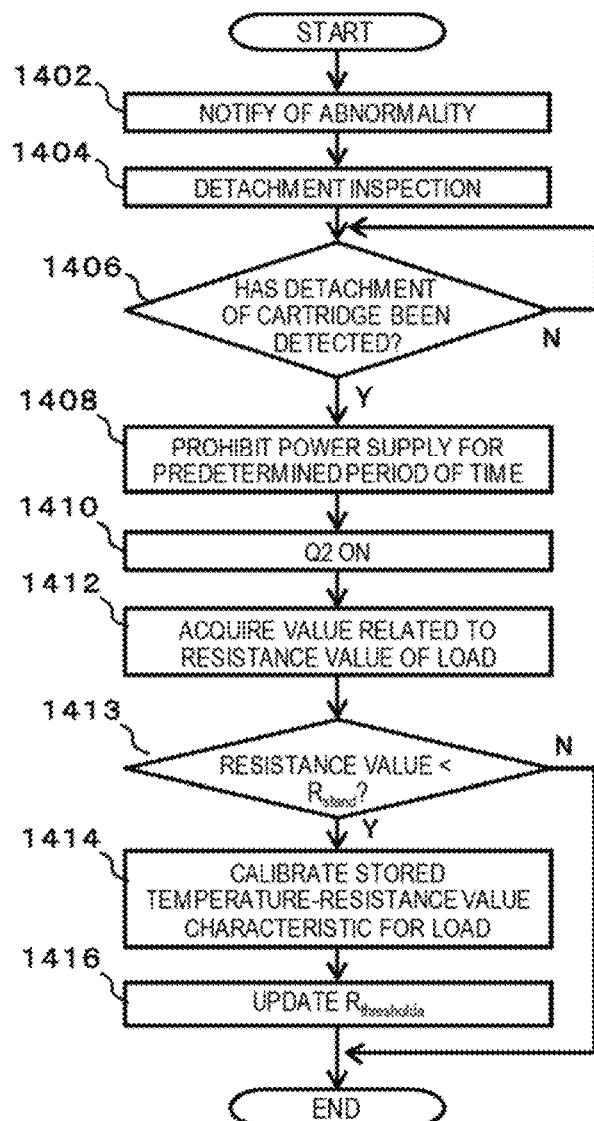

FIG. 14 is a flowchart of exemplary processing of calibrating a temperature-resistance value characteristic of the load according to an embodiment of the present disclosure, in light of a point pointed out in FIG. 13.

The processes in steps 1402 to 1412 are the same as the processes in steps 1002 to 1012 in FIG. 10, and description thereof is omitted.

In step 1413, the control unit 106 determines whether a resistance value (or a voltage value, a current value, or the like related to the resistance value) of the load 132 at the room temperature which is acquired in step 1412 is lower than "$R_{stand}$" (or a voltage value, a current value, or the like corresponding to this) shown in FIG. 13.

When the resistance value of the load 132 is lower than "$R_{stand}$" ("Y" in step 1413), the process proceeds to step 1414. The processes in steps 1414 and 1416 are the same as the processes in steps 1014 and 1016 in FIG. 10, and description thereof is omitted.

When the resistance value of the load 132 is equal to or higher than "$R_{stand}$" ("N" in step 1413), the processes of steps 1414 and 1416 are not performed, and the process ends.

According to the present embodiment, the control unit 106 may determine whether to perform the calibration based on the predetermined condition, prior to the calibration of the stored temperature-resistance value characteristic. As described above, in an example, the predetermined condition may be that from correspondence between an output value of the sensor and an estimate of the temperature of the load 132 corresponding to the output value, it is determined that the temperature of the load 132 is estimated smaller than an actual value if the stored temperature-resistance value characteristic is not calibrated. The predetermined condition may be that the output value of the sensor is lower than the predetermined threshold. With these configurations, the calibration is performed only when the overheating state occurs if the temperature-resistance value characteristic is not calibrated. Accordingly, when it is not necessary to perform the calibration, such as when the measured initial resistance value of the load includes a slight error such as an error of the sensor, undesirable calibration can be prevented from being performed.

Figure 15:
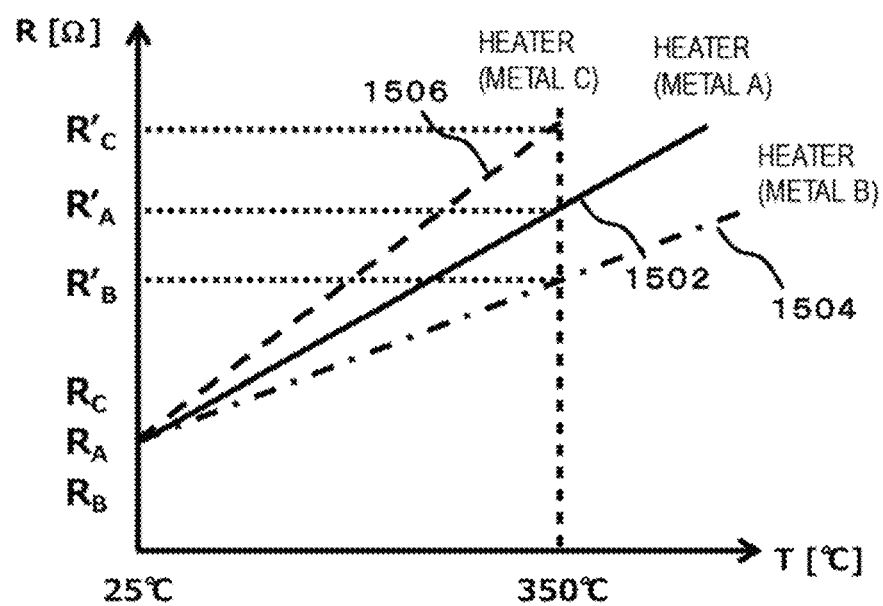

FIG. 15 is a graph showing an example of the temperature-resistance value characteristic of each of the different loads (heaters) 132 that are made of different metals. A solid line 1502, a dash dotted line 1504, and a dotted line 1506 indicate characteristics of a load 132A made of a metal A, a load 132B made of a metal B, and a load 132C made of a metal C, respectively. The different types of metals have different temperature coefficients of resistance, and different inclinations of the respective characteristics. Accordingly, as shown in the figure, even when the initial resistance values $R_A$, $R_B$, and $R_C$ of the load 132A, the load 132B, and the load 132C are the same value, the resistance values $R'_A$, $R'_B$, and $R'_C$ of the respective loads when the temperatures of the respective load reaches 350° C. are different from one another. As can be appreciated, when the cartridge 104A or the aerosol generating article 104B including a load made of a certain metal is replaced with the cartridge 104A or the aerosol generating article 104B including a load made of a different metal, it is necessary to update a threshold used for determining the insufficiency of the aerosol source. Note that the initial resistance values $R_A$, $R_B$, and $R_C$ of the load 132A, the load 132B, and the load 132C may be different values.

In such a case, in an example, the control unit 106 may measure the initial resistance value of the load 132 when the new cartridge 104A or the new aerosol generating article 104B is inserted into the aerosol generation device 100. Next, the control unit 106 may calculate a resistance threshold used for determining the insufficiency of the aerosol source based on the temperature-resistance value characteristic of the load 132 included in the cartridge 104A or the aerosol generating article 104B. In an example, the control unit 106 may acquire the information about the load 132 or the cartridge 104A or the aerosol generating article 104B such as the temperature-resistance characteristic by communicating with an external terminal such as a server. The control unit 106 may also acquire such information from the identification information included in an RFID tag of the load 132 or the cartridge 104A or the aerosol generating article 104B or the like, the identification information of the package of the cartridge 104A or the aerosol generating article 104B, the input by the user, and the like.

In an example, the aerosol generation device 100 may include the cartridge 104A that includes the load 132 and the storage unit 116A for storing the aerosol source or the aerosol generating article that includes the load 132 and the aerosol base material 116B for retaining the aerosol source, and the connecter that allows the attachment/detachment of the cartridge 104A or the insertion/extraction of the aerosol generating article 104B. In this example, the sensor is not necessarily included in the cartridge 104A or the aerosol generating article 104B. The control unit 106 may calibrate the stored temperature-resistance value characteristic based on the correspondence between a value obtained by subtracting a predetermined value (for example, a resistance value at a portion to which the cartridge 104A is connected) from an output value of the sensor and an estimate of the temperature of the load 132 corresponding to the output value. According to this configuration, the sensor for measuring the resistance value is provided to the main body 102. Accordingly, this can prevent increases in cost, weight, volume and the like of the cartridge 104A or the aerosol generating article 104B.

In an example, the aerosol generation device 100 may include the first circuit 202 used to cause the load 132 to atomize the aerosol source, and the second circuit 204 used to detect a value related to a resistance value of the load 132, connected to the first circuit 202 in parallel, and having an electric resistance value higher than that of the first circuit 202. According to this configuration, the aerosol generation device 100 includes a dedicated circuit (the second circuit 204) for measuring a voltage. Accordingly, this can reduce the electric power of the power supply 110 required for measuring the resistance value of the load 132.

In an example, the aerosol generation device 100 may include a circuit that electrically connects the power supply 110 and the load 132. The sensor may output a value of the voltage applied at least to a portion in the circuit where the voltage to be applied changes according to changes in temperature of the load 132. The control unit 106 may derive the electric resistance value of the load 132 based on a value of the voltage applied to the entire circuit and the output value of the sensor. According to this configuration, it is only required that only two voltage sensors are used, the two voltage sensors including a voltage sensor for measuring the voltage applied to the entire circuit and a voltage sensor for measuring the voltage applied to a portion where the voltage to be applied changes according to changes in temperature of the load 132. Accordingly, it is only required that the minimum required sensors are added to the existing device.

In an example, the aerosol generation device 100 may include the conversion unit 208 that converts the output voltage of the power supply 110 and outputs the converted voltage to apply it to the entire circuit. To derive the electric resistance value of the load 132, the control unit 106 may control the conversion unit 208 to apply a constant voltage to the entire circuit. With this configuration, the use of the converter enables the control unit 106 to control the voltage applied to the entire circuit to be constant when the resistance value is measured. Accordingly, the likelihood of the resistance value to be measured is improved.

In an example, the aerosol generation device 100 may include the power supply 110, the load 132 that generates heat upon receipt of electric power using the heat from the power supply 110 and atomizes an aerosol source and has a temperature-resistance value characteristic in which an electric resistance value changes in response to a temperature, the memory 114 that stores the temperature-resistance value characteristic, the sensor 112 that outputs a value related to the resistance value of the load 132, and the control unit 106 configured to perform a predetermined control based on the temperature-resistance value characteristic. The control unit 106 may calibrate a value (a constant, a variable, a threshold, or the like) related to the predetermined control based on correspondence between an output value of the sensor 112 and an estimate of the temperature of the load 132 corresponding to the output value.

In the above description, the third embodiment of the present disclosure has been described as an aerosol generation device and a method of actuating the aerosol generation device. However, it will be appreciated that the present disclosure, when being executed by a processor, can be implemented as a program that causes the processor to perform the method or as a computer readable storage medium storing the same program.

The embodiments of the present disclosure have been described thus far, and it should be understood that these embodiments are only illustration, and do not limit the scope of the present disclosure. It should be understood that modification, addition, alteration and the like of the embodiments can be properly performed without departing from the gist and the scope of the present disclosure. The scope of the present disclosure should not be limited by any of the aforementioned embodiments, but should be specified by only the claims and the equivalents of the claims.

REFERENCE SIGNS LIST 100A, 100B . . . aerosol generation device, 102 . . . main body, 104A . . . cartridge, 104B . . . aerosol generating article, 106 . . . control unit, 108 . . . notifying unit, 110 . . . power supply, 112A to 112D . . . sensor, 114 . . . memory, 116A . . . storage unit, 116B . . . aerosol base material, 118A, 118B . . . atomizing unit, 120 . . . air intake channel, 121 . . . aerosol flow path, 122 . . . mouthpiece unit, 130 . . . retention unit, 132 . . . load, 134 . . . circuit, 202 . . . first circuit, 204 . . . second circuit, 206, 210, 214 . . . FET, 208 . . . conversion unit, 212 . . . resistor, 216 . . . diode, 218 . . . inductance, 220 . . . capacitor, 702 . . . comparator, 704 . . . A/D converter, 706, 708 . . . amplifier, 710 . . . power supply, 902, 904, 906, 1302, 1304, 1306, 1502, 1504, 1506 . . . temperature-resistance value characteristic

The invention claimed is:

1. An aerosol generation device, comprising:
a power supply;
a load that generates heat upon receipt of electric power from the power supply and atomizes an aerosol source using the heat, and has a temperature-resistance value characteristic in which an electric resistance of the load value changes in response to a temperature;
a memory configured to store the temperature-resistance value characteristic;
a sensor configured to output a value related to a resistance value of the load;
processing circuitry configured to control supply of electric power from the power supply to the load,
calibrate the stored temperature-resistance value characteristic based on correspondence between an output value of the sensor when electric power sufficient for aerosol generation is supplied to the load and a temperature causing the aerosol generation, and
not calibrate the stored temperature-resistance value characteristic when the output value of the sensor when the electric power sufficient for the aerosol generation is supplied to the load is equal to or higher than a threshold or when a change amount in the output value of the sensor when predetermined electric power is supplied to the load is equal to or higher than a threshold;
a cartridge that includes the load and stores the aerosol source or an aerosol generating article that includes the load and an aerosol base material that retains the aerosol source; and
a connecter that allows attachment and detachment of the cartridge or insertion and extraction of the aerosol generating article,
wherein the processing circuitry is further configured to calibrate the stored temperature-resistance value characteristic only when detecting the detachment of the cartridge from the connecter or the extraction of the aerosol generating article from the connecter.

2. The aerosol generation device according to claim 1, wherein the processing circuitry is further configured to
calibrate the stored temperature-resistance value characteristic based on correspondence between the output value of the sensor before the load generates aerosol and a room temperature.

3. The aerosol generation device according to claim 2, wherein the processing circuitry is further configured to
calibrate the stored temperature-resistance vale characteristic based on the correspondence between the output value of the sensor before the load generates the aerosol and the room temperature in response to a predetermined condition by which it is determined that the temperature of the load is the room temperature is established.

4. The aerosol generation device according to claim 3, wherein
the predetermined condition is that a predetermined period of time has elapsed since previous aerosol generation.

5. The aerosol generation device according to claim 3, comprising:
wherein the predetermined condition is that a predetermined period of time has elapsed since the attachment of the cartridge to the connecter or the insertion of the aerosol generating article into the connecter.

6. The aerosol generation device according to claim 2, wherein the processing circuitry is further configured to
supply predetermined electric power from the power supply to the load, the predetermined electric power being smaller than electric power required to increase the temperature of the load to a temperature at which the load is capable of generating the aerosol, and
calibrate the temperature-resistance value characteristic based on the output value of the sensor while the predetermined electric power is supplied to the load.

7. The aerosol generation device according to claim 1, wherein the processing circuitry is further configured to
control supply of electric power from the power supply to the load, and
calibrate the stored temperature-resistance value characteristic based on correspondence between the output value of the sensor when electric power sufficient for aerosol generation is supplied to the load and in a steady state at a value other than a room temperature, and a temperature causing the aerosol generation.

8. The aerosol generation device according to claim 1, wherein
the temperature and the electric resistance value of the load are in a proportional relationship, and
the processing circuitry is further configured to calibrate an inclination and an intercept of the stored temperature-resistance value characteristic based on correspondence between the output value of the sensor before the load generates aerosol and a room temperature and correspondence between the output value of the sensor when electric power sufficient for aerosol generation is supplied to the load and a temperature causing the aerosol generation.

9. The aerosol generation device according to claim 1, wherein the processing circuitry is further configured to
determine whether to perform a calibration based on a predetermined condition, prior to the calibration of the stored temperature-resistance value characteristic.

10. The aerosol generation device according to claim 9, comprising:
wherein the processing circuitry is further configured to store a resistance value of the cartridge detached from the connecter or a resistance value of the aerosol generating article extracted from the connecter, and
wherein the predetermined condition is that the resistance value stored by the processing circuitry is different from the resistance value of the cartridge newly attached to the connecter or the resistance value of the aerosol generating article newly inserted into the connecter.

11. The aerosol generation device according to claim 9, wherein
the predetermined condition is that from the correspondence between the output value of the sensor and an estimate of the temperature of the load corresponding to the output value, it is determined that the temperature of the load is estimated smaller than an actual value when the stored temperature-resistance value characteristic is not calibrated.

12. The aerosol generation device according to claim 9, wherein
the predetermined condition is that the output value of the sensor is smaller than a predetermined threshold.

13. The aerosol generation device according to claim 1, comprising:
wherein the sensor is not included in the cartridge or the aerosol generating article, and
wherein the processing circuitry is further configured to calibrate the stored temperature-resistance value characteristic based on correspondence between a value obtained by subtracting a predetermined value from the output value of the sensor and the estimate of the temperature of the load corresponding to the output value.

14. The aerosol generation device according to claim 1, comprising:
a first circuit configured to cause the load to atomize the aerosol source; and
a second circuit configured to detect a value related to a resistance value of the load, connected to the first circuit in parallel, and having an electric resistance value higher than an electric resistance value of the first circuit.

15. The aerosol generation device according to claim 1, further comprising:
a third circuit that electrically connects the power supply and the load,
wherein the sensor outputs at least a value of a voltage applied to a portion in the third circuit where the voltage to be applied changes according to changes in the temperature of the load, and
wherein the processing circuitry is further configured to derive the electric resistance value of the load based on a value of a voltage applied to an entire circuit and the output value of the sensor.

16. The aerosol generation device according to claim 15, wherein the processing circuitry is further configured to
convert an output voltage of the power supply and output the converted voltage to apply it to the entire circuit, and
apply a constant voltage to the entire circuit to derive the electric resistance value of the load.

* * * * *